US012710419B2

(12) United States Patent
Yao et al.

(10) Patent No.: US 12,710,419 B2
(45) Date of Patent: Aug. 18, 2026

(54) 3D SENSORS FOR SIMULTANEOUS DETECTION OF BIOELECTRONIC AND BIOMECHANICAL SIGNALS IN TISSUE

(71) Applicant: UNIVERSITY OF MASSACHUSETTS, Boston, MA (US)

(72) Inventors: Jun Yao, Boston, MA (US); Hongyan Gao, Boston, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 607 days.

(21) Appl. No.: 18/306,664

(22) Filed: Apr. 25, 2023

(65) Prior Publication Data

US 2023/0341386 A1 Oct. 26, 2023

Related U.S. Application Data

(60) Provisional application No. 63/334,426, filed on Apr. 25, 2022.

(51) Int. Cl.
*G01N 33/543* (2006.01)
*G01N 27/327* (2006.01)

(52) U.S. Cl.
CPC ... *G01N 33/54373* (2013.01); *G01N 27/3278* (2013.01)

(58) Field of Classification Search
CPC ......... G01N 33/54373; G01N 27/3278; G01N 2203/0051; G01N 2203/0623; G01R 29/22
See application file for complete search history.

(56) References Cited

U.S. PATENT DOCUMENTS

2012/0068156 A1* 3/2012 Koley .................... G01N 27/26 257/14

OTHER PUBLICATIONS

Luo et al., "Synthesis of Long Indium Nitride Nanowires with Uniform Diameters in Large Quantities," small 2005, 1, No. 10, 1004-1009 (Year: 2005).*
Brelje et al., "Cardiac Muscle Tissue", online Histology Guide, 2025, https://histologyguide.com/slideview/MH-054-cardiac-muscle/04-slide-1.html?b=c_1_1_3_29360_663_2.658_default (Year: 2025).*
"Neurons" online article, Beckman-Coulter, 2025, https://www.beckman.com/resources/cell-types/neurons#:~:text=The%20circular%20cell%20body%2C%20or,action%20potentials%20are%20generated%20here. (Year: 2025).*
Wilson et al., "InN Nanowires Based Multi-Modal Environmental Sensors," Conference: Sensors, 2013 IEEE (Year: 2013).*

(Continued)

*Primary Examiner* — Alexander S Noguerola
(74) *Attorney, Agent, or Firm* — Thomas | Horstemeyer, LLP

(57) ABSTRACT

The present disclosure presents biosensor devices, systems, and related methods. One such biosensor device comprises a substrate; a semiconductive channel member suspending between a pair of contacts on the substrate, wherein the semiconductive channel member comprises a convex protruding channel structure; and wherein the convex protruding channel structure is configured to detect both electrical and mechanical cellular responses. Other devices, systems, and methods are also presented.

20 Claims, 34 Drawing Sheets

(56) References Cited

OTHER PUBLICATIONS

Eschermann et al., “Action potentials of HL-1 cells recorded with silicon nanowire transistors,” Appl. Phys. Lett. 95, 083703 (2009) (Year: 2009).*
Cohen-Karni et al., “Flexible electrical recording from cells using nanowire transistor arrays,” PNAS | May 5, 2009 | vol. 106 | No. 18 | 7309-7313 (Year: 2009).*
Rajan et al., “Performance limitations for nanowire/nanoribbon biosensors,” WIREs Nanomed Nanobiotechnol 2013, 5:629-645. doi: 10.1002/wnan.1235 (Year: 2013).*
Cohen-Karni et al., “Graphene and Nanowire Transistors for Cellular Interfaces and Electrical Recording,” Nano Lett. 2010, 10, 1098-1102 (Year: 2010).*
Deng et al., “Wrinkled, rippled and crumpled graphene: an overview of formation mechanism, electronic properties, and applications ,” Materials Today vol. 19, No. 4 May 2016 (Year: 2016).*
Tian et al., “Microporous nanowire nanoelectronics scaffolds for synthetic tissues,” Nature Materials | vol. 11 | Nov. 2012 (Year: 2012).*

* cited by examiner

3D SENSORS FOR SIMULTANEOUS DETECTION OF BIOELECTRONIC AND BIOMECHANICAL SIGNALS IN TISSUE

CROSS-REFERENCE TO RELATED APPLICATION

This application claims priority to U.S. provisional application entitled, "3D Sensors for Simultaneous Detection of Bioelectric and Biomechanical Signals in Tissue," having Ser. No. 63/334,426, filed Apr. 25, 2022, which is entirely incorporated herein by reference.

STATEMENT REGARDING FEDERALLY SPONSORED RESEARCH OR DEVELOPMENT

This invention was made with government support under Award No. CBET-1844904 awarded by the National Science Foundation. The government has certain rights in the invention.

BACKGROUND

The intimate interrelation between bioelectrical and biomechanical processes in cells and tissue often makes it important to study their correlated dynamics. For example, the excitation-contraction (EC) coupling in cardiomyocytes carries crucial information for identifying cardiac disease mechanisms and hence potential drug targets. Despite the importance, it remains challenging to simultaneously measure the two processes. Traditional optical methods relied on fluorescence labeling to indicate bioelectrical signals and morphological tracing to detect biomechanical behaviors. The two methods were combined to study EC dynamics in individual cells, revealing information otherwise missed from single-parameter measurement. However, they are limited in the scalable tracking of fast kinetics in 3D tissue due to reduced temporal resolution and accessibility; and molecular labeling may also compromise cell contractility or induce toxicity.

Electrical sensors can enable label-free, multiplexed interrogation at high temporal resolution. They can be further integrated on flexible and porous scaffolds to innervate the tissue, retrieving deep-tissue information that is less accessible by other techniques. Nevertheless, current electrical sensors such as microelectrode and transistor arrays are limited to probing a single property of an electrical or mechanical response only. Efforts have been made recently to combine them with complementary sensors for the simultaneous measurement, although the heterogeneity leads to considerable challenges in synchronization or scalability. For example, a nanopatterned microelectrode was fabricated on an atomic force microscope (AFM) tip for a force-electrogram recording in a cell, which was limited in scalability and accessibility with the single cantilever in an AFM setup. Microelectrodes and pairs of interdigitated electrodes were also combined for synchronized recordings of electrical and mechanical activities in cardiac tissue. However, the pair of interdigitated electrodes for motion tracking through impedance measurement were of a large size, limiting the measurement to a single- or few-device scale with a low resolution at the tissue level.

Overall, the strategy of combining two types of sensors inevitably leads to heterogeneity in integration and/or signal acquisition, which further limits the scalability and spatial resolution (i.e., increased space occupation with two sensors). The latter introduces not only a challenge in achieving cellular-resolution recording, but also a spatial discrepancy in acquired signals and hence inaccuracies when studying correlated dynamics. In addition, it also increases the invasiveness to biological tissue.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 2A shows 8-channel recordings from cultured cardiomyocytes; FIG. 2B shows zoomed-in signals from the dashed box in FIG. 2A; FIG. 2C shows a zoomed-in signal in one period.

FIG. 3A shows a schematic of blebbistatin effect on inhibiting cell contraction; FIG. 3B shows electrical recordings from cardiomyocytes before (left) and after (right) adding blebbistatin; FIG. 3C demonstrates an evolution in amplitude of the mechanical response (black) and AP (gray) after adding blebbistatin; FIG. 3D shows a schematic of lidocaine effect on blocking Na+ channels; FIG. 3E shows recorded electrical signals before (orange) and after (blue) adding lidocaine; FIG. 3F shows superimposed signals before (gray) and after (dark) adding lidocaine, with the orange and blue curves representing the corresponding mean waveforms; FIG. 3G shows recorded electrical signals before (left) and after (right) adding isradipine, which blocks the $Ca^{2+}$ channels (inset schematic); FIG. 3H shows zoomed-in signals in FIG. 3G over time (indicated by arrows). The inset shows zoom-in AP in the dashed box; and FIG. 3I shows the evolution in amplitude of the mechanical (black) and AP (gray) signals after adding isradipine.

FIG. 4B shows (simulated) average net strain ($\overline{\Delta\varepsilon}$) induced in the nanowire with respect to e and the inset shows strain distribution along the nanowire at different e; FIG. 4C shows the evolution of local amplitudes (as represented by different colors in original image) and vectors (arrows) of cellular motion at the device region during a contractile cycle (area~35×35 $\mu m^2$); FIG. 4D shows the correlation between the electrical sensing signal (top), average amplitude ($\overline{D}$) (middle) and average angle $\overline{\theta}$ (bottom) of cellular motion at the sensor region; FIG. 4E shows local amplitudes (as represented by different colors in original image) and vectors (arrows) of cellular motion at another device region; and FIG. 4F shows corresponding electrical sensing signal (top), $\overline{D}$ (middle), and $\overline{\theta}$ (bottom) in FIG. 4E.

DETAILED DESCRIPTION

Figure 1A:
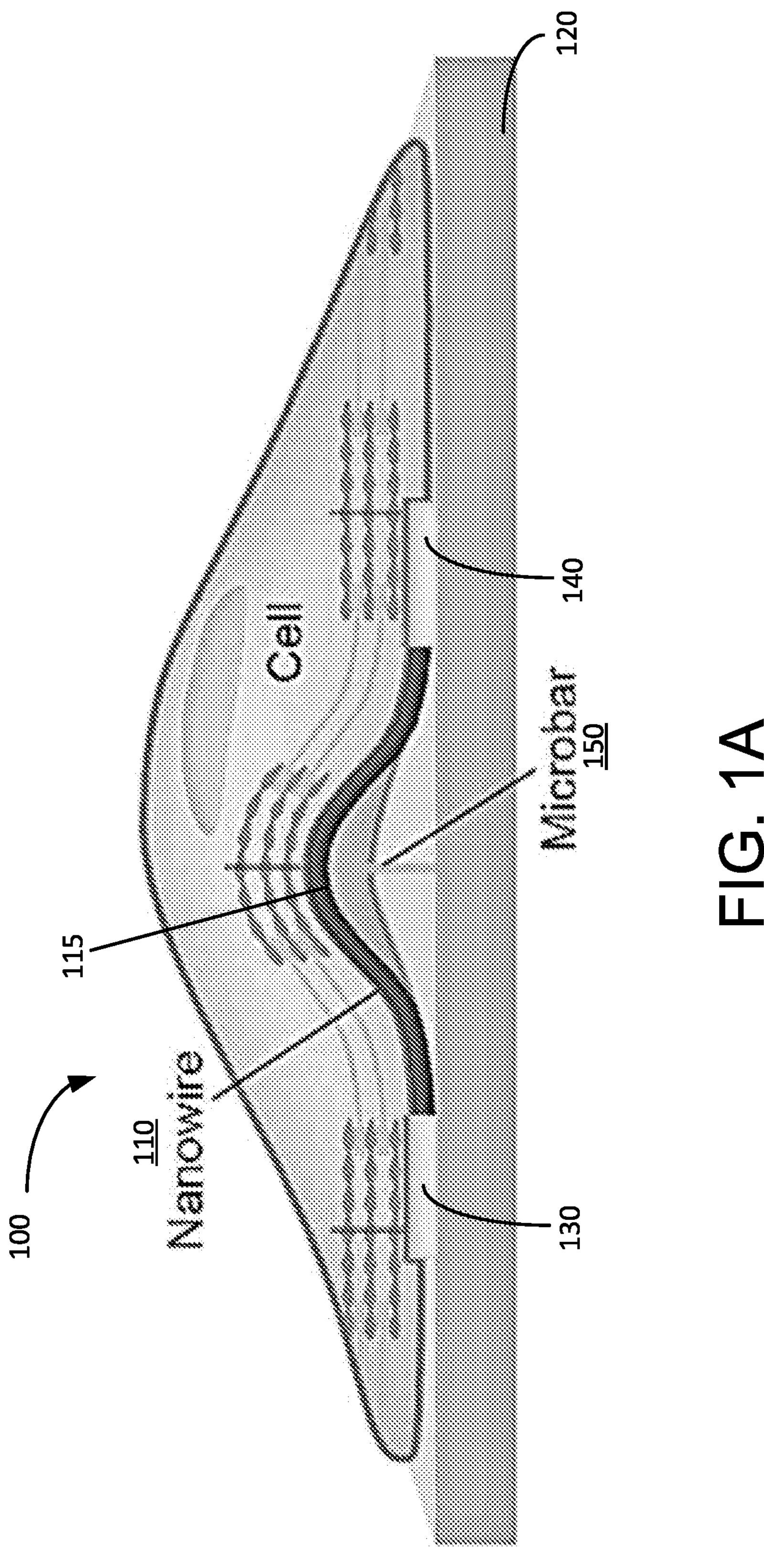
FIG. 1A shows a schematic of an exemplary biosensor structure and cell-sensor interface in accordance with embodiments of the present disclosure.

The present disclosure describes various systems, apparatuses, and methods for biosensing of electrical and mechanical cellular responses.

Cardiac diseases are among the leading causes of human morbidity and mortality. In vitro cardiac models offer promising platforms for disease mechanism study, drug tests, and regenerative medicine. The excitation-contraction dynamics are the most important physiological parameters for assessing developmental state, which require the simultaneous measurements of both electrical and mechanical cellular responses in a scalable way. However, existing biosensors such as microelectrode arrays and microposts can only interrogate one response at a time. Optical imaging is limited in deep-tissue accessibility and may also induce phototoxicity.

Accordingly, the present disclosure demonstrates integrated nanoelectronic biosensors capable of simultaneously probing electrical and mechanical cellular responses. In accordance with embodiments of the present disclosure, an exemplary biosensor 100 is configured from a 3D semiconducting channel member 110 (e.g., silicon nanowire) that extends across a substrate 120 and is connected to drain and source contacts 130,140 on the substrate to form a nanotransistor sensing device with its conduction channel 115 protruding out of the plane. The protruding feature 115 promotes not only a tight seal with the cell for detecting action potentials (AP) via the field effect but also a close mechanical coupling for detecting cellular force via the piezoresistive effect. In accordance with embodiments of the present disclosure, arrays of nanotransistors can be integrated to realize label-free, sub-millisecond, and scalable interrogation of correlated cell dynamics, showing advantages in tracking and differentiating cell/tissue states in drug studies. An exemplary sensor 100 can further decode vector information in cellular motion, transcending the typical scalar information acquired at the tissue level and hence offering a new tool for cell mechanics studies. The two-in-one sensor 100 offers not only a promising candidate for assembling advanced bioelectronic platforms but also an equivalent scaling to minimize invasiveness to tissue models.

In comparison, previous bioelectronic sensors can only detect one type of signal from the tissue. They are limited to one signal and incapable of studying the dynamic correlation between different signals. Combining different types of sensors to perform simultaneous recording inevitably leads to challenges in integration and synchronization, which also adds to invasiveness to tissue. However, an exemplary sensor 100 of the present disclosure can simultaneously detect both bioelectrical and biomechanical signals from tissue, enabling the study of the dynamic correlation between them without increasing the difficulty in integration, synchronization, and invasiveness.

Figure 1B:
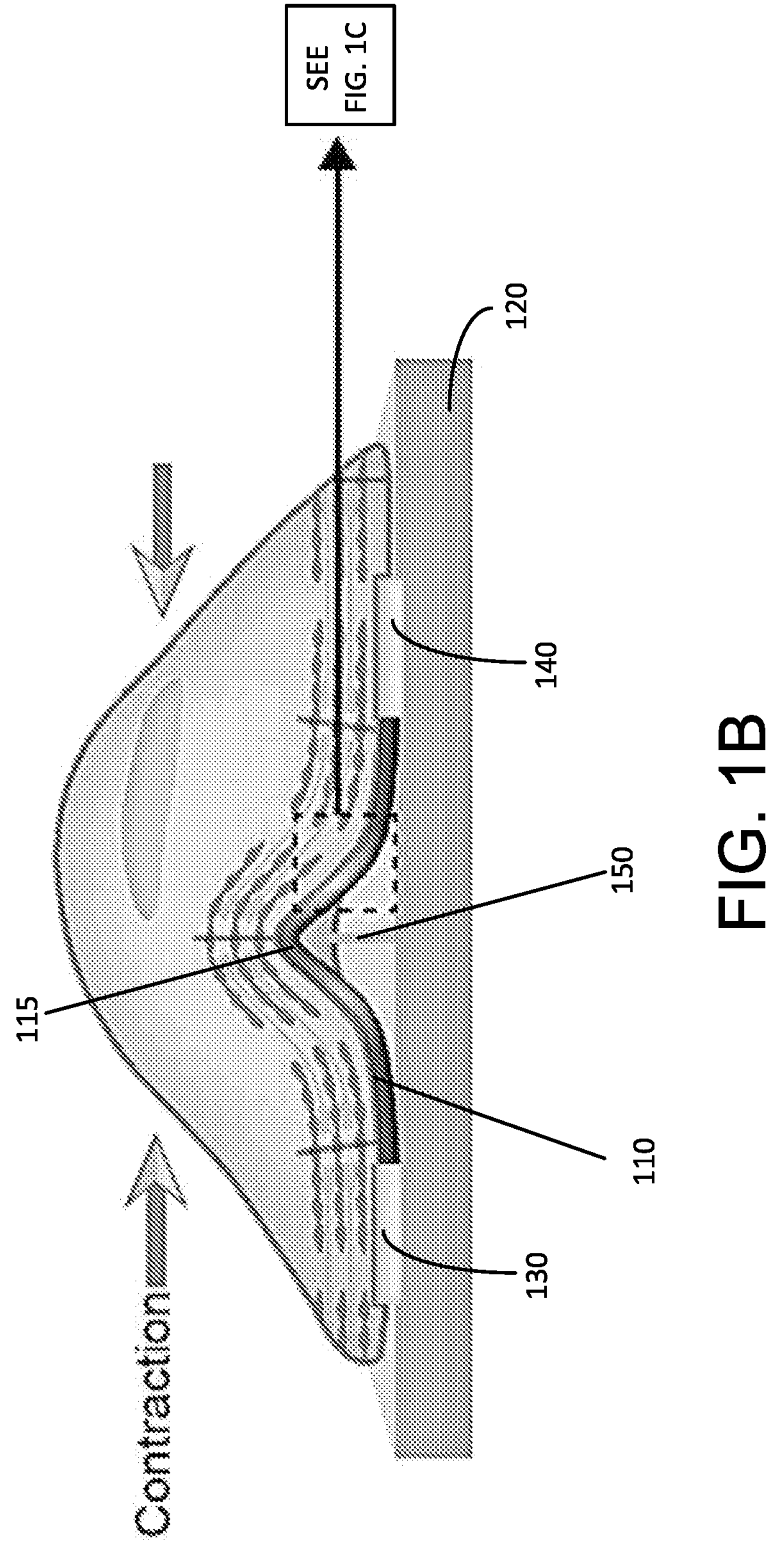
FIG. 1B shows a schematic of a cell-sensor coupling during a contractile process in accordance with embodiments of the present disclosure.
Figure 1C:
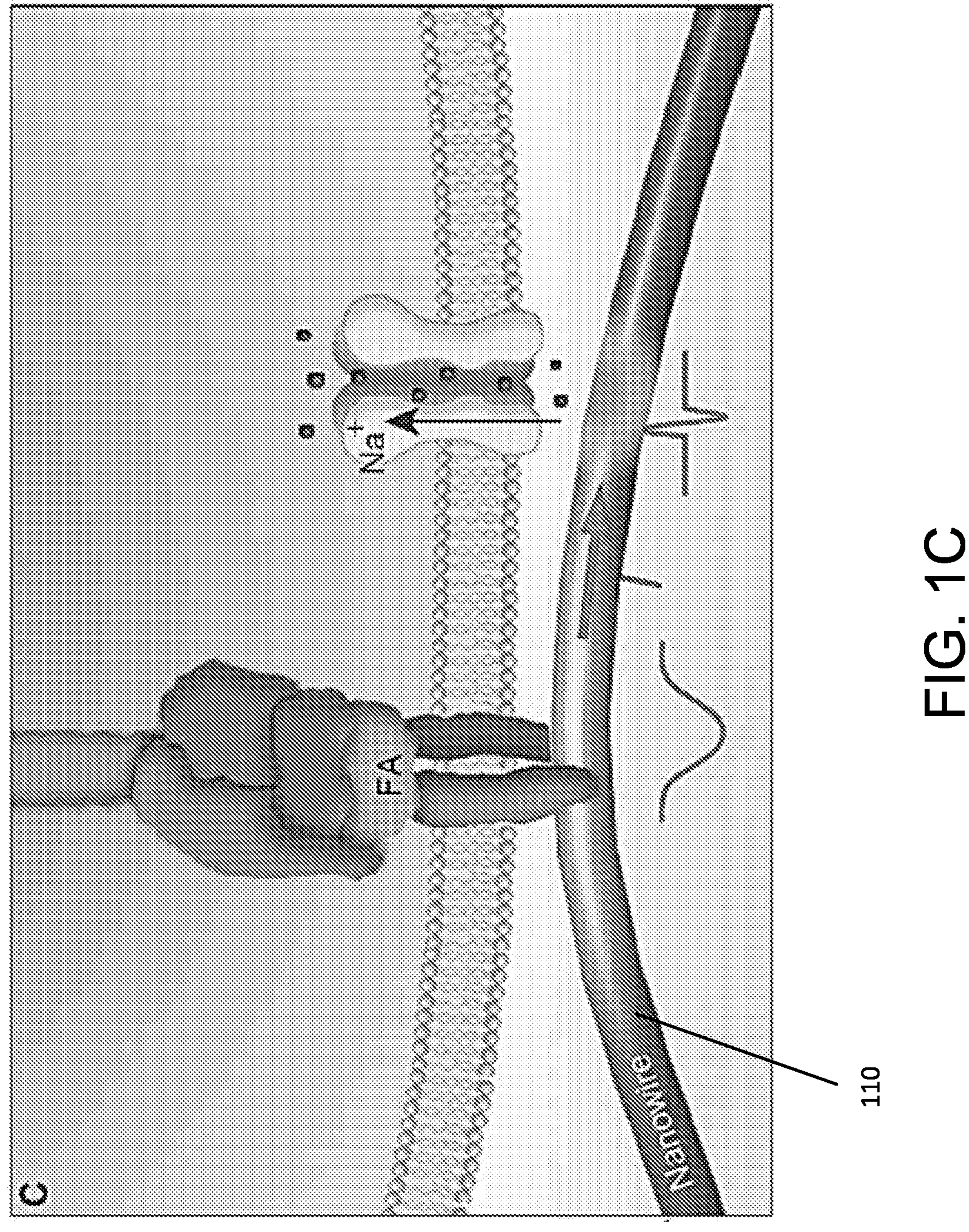
FIG. 1C shows a schematic of the electrical coupling and mechanical coupling between the semiconducting member of an exemplary biosensor and a cell for the simultaneous detection of cellular force and electrical action potential (AP) in accordance with embodiments of the present disclosure.

In various embodiments, an exemplary 3D nanotransistor sensing device 100 can be constructed from a nanowire to converge sensing functionalities, such that the device 100 has a convex protruding channel structure 115 by translating a semiconducting silicon (Si) nanowire across a mechanical support structure 150 (e.g., a microscale bar or microbar), as shown in FIG. 1A. The drain and source contacts 130, 140 on the substrate and the mechanical support structure 150 (e.g., microbar) supporting the apex of the semiconducting channel member 110 (e.g., Si nanowire) form a triangular configuration to confer structural stability. The geometrical freedom in the suspended nanowire allows for the translation of cellular force into mechanical deformation or strain change in the semiconducting channel member (e.g., Si nanowire), as shown in FIGS. 1B and 1C, which can be electrically detected through the piezoresistive effect. In particular, FIG. 1C shows a schematic of the electrical coupling and mechanical coupling (e.g., through integrins of focal adhesion (FA)) between the nanowire and cell for the simultaneous detection of cellular force and AP. Thus, as shown in FIG. 1C, the nanotransistor sensing device 100 can detect AP through the field effect. As biomechanical and bioelectrical processes can fall into different frequency domains, both can be electrically detected and differentiated in a single biosensor device 100.

Some unique advantages can be inferred. For example, for an embodiment utilizing a Si nanowire as the semiconducting channel member 110, the suspended nanowire geometry resembles biofilaments in an extracellular matrix, to which cells attach. Therefore, the sensor geometry may facilitate cell attachment for signal transductions. Second, Si nanowire has a giant piezoresistance effect, offering enhanced force sensitivity down to tens of pN. This is crucial for resolving cellular forces at nN or sub-nN level. It is noted that Si nanowire has a strength for sustaining μN force, providing mechanical robustness against cellular force. Third, the 3D protruding feature can tighten the cell-device seal to improve the detection of electrical activities.

In various embodiments, nanotransistor arrays can be constructed using a scalable nanowire 3D assembly based on a 'combing' technique. Electrical contacts were defined and passivated by standard microfabrication. Briefly, planar Si nanowire arrays were first assembled by a deterministic 'combing' technique on a Si substrate (covered with 600 nm $SiO_2$). A thin layer of poly(methyl methacrylate) (PMMA, Microchem 950 C2) with the thickness of ~100 nm was spin-coated onto the assembled nanowires, which was then peeled off using water intercalation to carry the embedded nanowires (step-I). A soft stamp (~1 mm thick) made from polydimethylsiloxane (PDMS, Sylgard 184, 10:1) was used to pick up the peeled-off PMMA layer and transferred onto a Si substrate with predefined SU-8 (Microchem 2002) microbar arrays (height ~1.4 μm) defined by electron beam lithography (step-II). The PMMA layer was release from the PDMS stamp (step-III), assisted by a thermal treatment (100° C., 2 min). The PMMA layer was dissolved in acetone, leaving the nanowires on the microbars to form the 3D structures (step-IV). Electrical contacts (Cr/Pd, 3/70 nm) were subsequently defined by using standard photolithography, metal evaporation, and lift-off processes (step-V). The contacts and interconnects were further passivated with a Si3N4 layer (~90 nm) to prevent current leakage in solution (step-VI).

In an alternative assembly technique, the nanowires were initially aligned randomly across the entire substrate using a contact printing method. Then they were peeled off and transferred onto pre-defined SU-8 microbar arrays (top panel) following the standard procedures. Arrays of photoresist stripes (Microchem LOR 5A+S1805) were then lithographically patterned at the assembly sites to serve as protective masks (bottom panel). Nanowires outside the mask region were etched by reactive ion etch ($SF_6/O_2$=20/50 sccm; 100 W, 30s), with the photoresist subsequently dissolved (PG remover, Microchem).

Figure 1D:
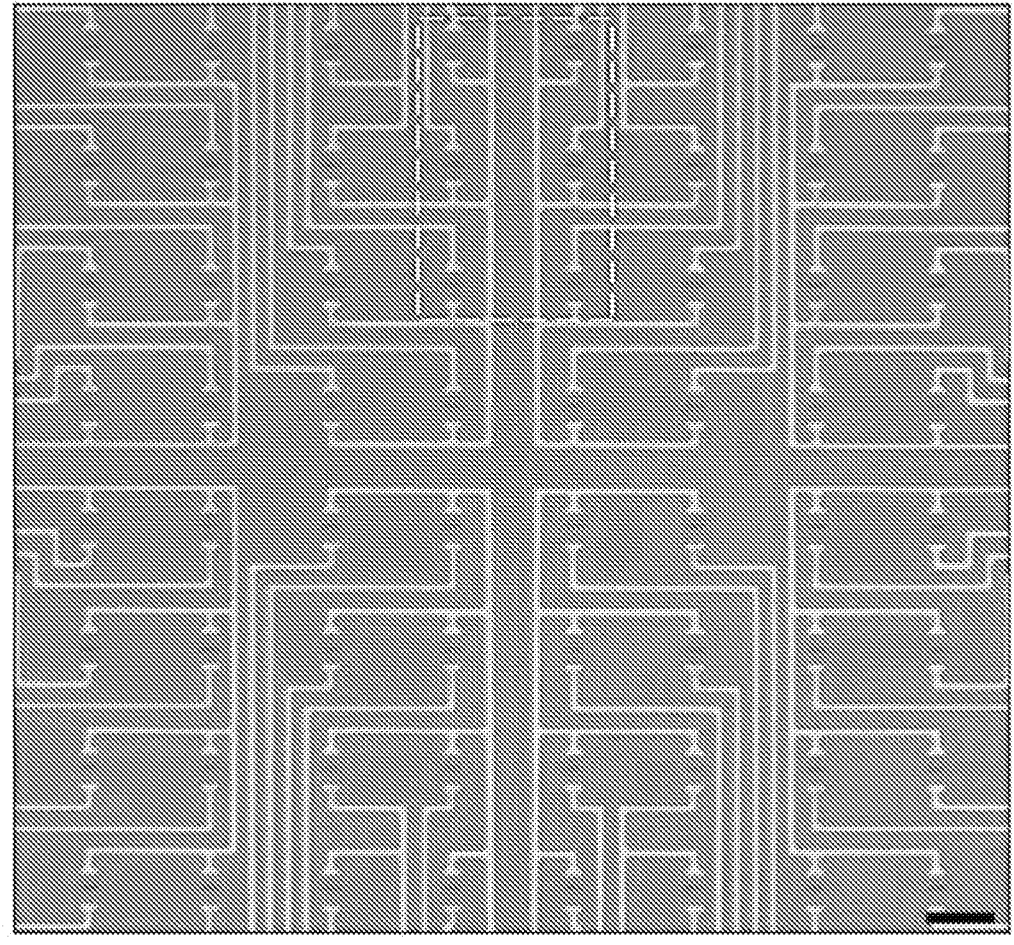
FIG. 1D shows an optical image of a fabricated 8×8 biosensor array in accordance with embodiments of the present disclosure.
Figure 1E:
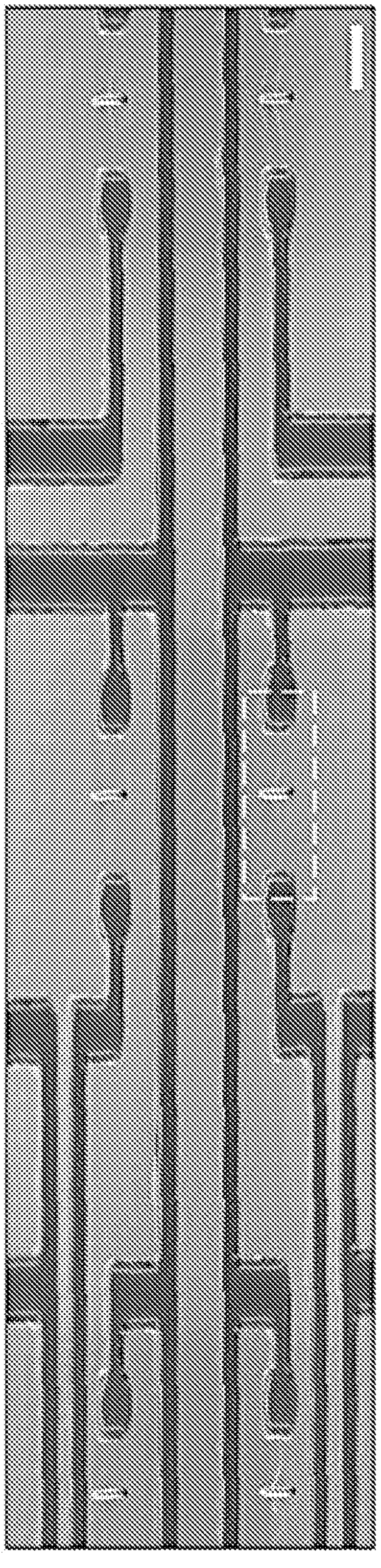
FIG. 1E shows a scanning electron microscope (SEM) image of a 2×3 biosensor array corresponding to devices in the dashed box in FIG. 1D.
Figure 1F:
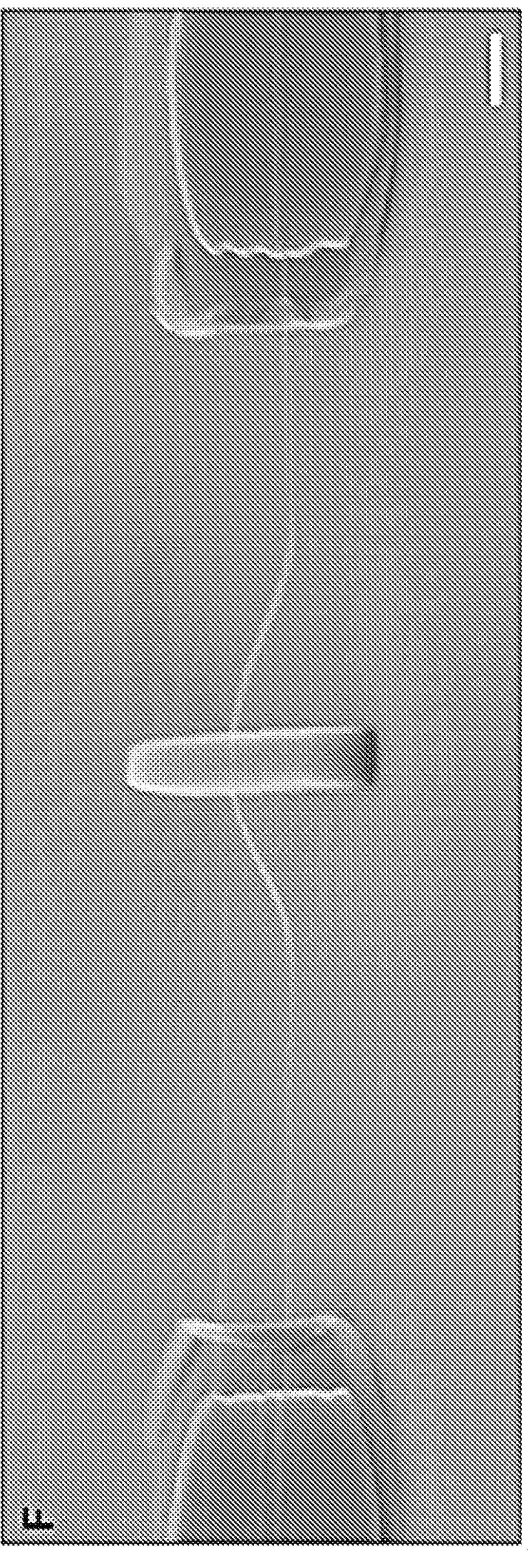
FIG. 1F shows an SEM image of a biosensor device corresponding to the dashed box in FIG. 1E.

As shown in FIG. 1D, a matrix of 8×8 nanotransistors were integrated in an area of ~0.8×0.8 $mm^2$. The device features two symmetrical nanowire arms suspended across a microbar (~1.4 μm high), spanning an average distance of 7.8±0.9 μm, as shown in FIGS. 1E and 1F. With a nanowire diameter ~30-50 nm, the nanotransistor occupies a projected area <0.4 $\mu m^2$, much smaller than typical microelectrodes or strain sensors used in tissue recording. A device yield of ~63-93% was achieved. Compensated by the small device size, high-density integration achieving cellular or subcellular resolution is feasible.

Electrical characterizations were performed in the devices to reveal the potential for recording electrical and mechanical cellular responses. The as-assembled nanowire is estimated to experience a maximal strain ~0.3%, which is in the elastic region and far below the fracture limit. As a result, the sensitivity to field potential (4.2±1.0 μS/V), characterized by water-gate response, was unaffected and close to that in unstrained Si-nanowire transistors capable of detecting AP.

For simulation (by finite element analysis using Abaqus/Standard (2020)), the nanotransistor was placed at the central region of a PDMS matrix (20×20×2 $\mu m^3$, W×L×H) with uniform pressure applied from the top. The elastic modulus of the SU-8, PDMS, and Si nanowire was taken as 2.0 GPa, 2.6 MPa, and 188 GPa, respectively. The average slope or conductance change per kP, is $k1=(\Delta G)/P=(9.6\pm1.3)\times10^{-5}$ $kPa^{-1}$. The slope or net strain εΔ per kP, is $k2=\Delta\varepsilon/P=-1.26\times10^{-7}$ $kPa^{-1}$. Therefore, the average gauge factor is $$g=\frac{\left(\frac{\Delta R}{R}\right)}{\Delta\varepsilon}=-\frac{\left(\frac{\Delta G}{G}\right)}{\Delta\varepsilon}=-\frac{k1}{k2}=(7.6\pm1.0)\times10^{2}.$$

For a resolvable pressure of 2 kPa (A) with corresponding strain of $-2.5\times10^{-7}$, the equivalent force exerted along the nanowire axis is $$F=E\times\Delta\varepsilon\times\left(\frac{\pi d^2}{4}\right)=33\ pN,$$

where E, d correspond to elastic modulus (188 GPa) and diameter (30 nm) of Si nanowire, respectively.

Meanwhile, mechanical testing and simulation revealed an average gauge factor of $7.6\pm1.0\times10^2$ in the nanowires, much larger than typical values of 2-135 in conventional materials. This enhanced mechanical sensitivity is consistent with the previously observed giant piezoresistance, constituting a unique advantage in improving force detection. Specifically, the estimated force resolution ~33 pN was commensurate with the strength of protein bonds in cell adhesion and much smaller than typical contractile forces (e.g., 1-100 nN) revealed by micropost arrays, indicating the capability in the sensor for tracking minute cellular force. The devices showed good uniformity in responding to both compressive and tensile strain for integrated signal analysis.

Specifically, the devices were fabricated on the central region of a rectangular Si substrate (4 cm×7 cm). Both the lateral edges (along the width) of the substrate were mechanically fixed. A sapphire bead (3 mm diameter) was placed beneath of the substrate center and displaced by a micrometer in the vertical direction to bend the substrate. A decrease in conductance was observed with the increase in the vertical displacement, ΔZ. The average slope was $-(3.5\pm0.76)\times10^{-3}$ $\mu m^{-1}$. The linear decrease in conductance at increasing tensile strain was consistent with test results, where compressive strain yielded conductance increase.

Figure 2A:
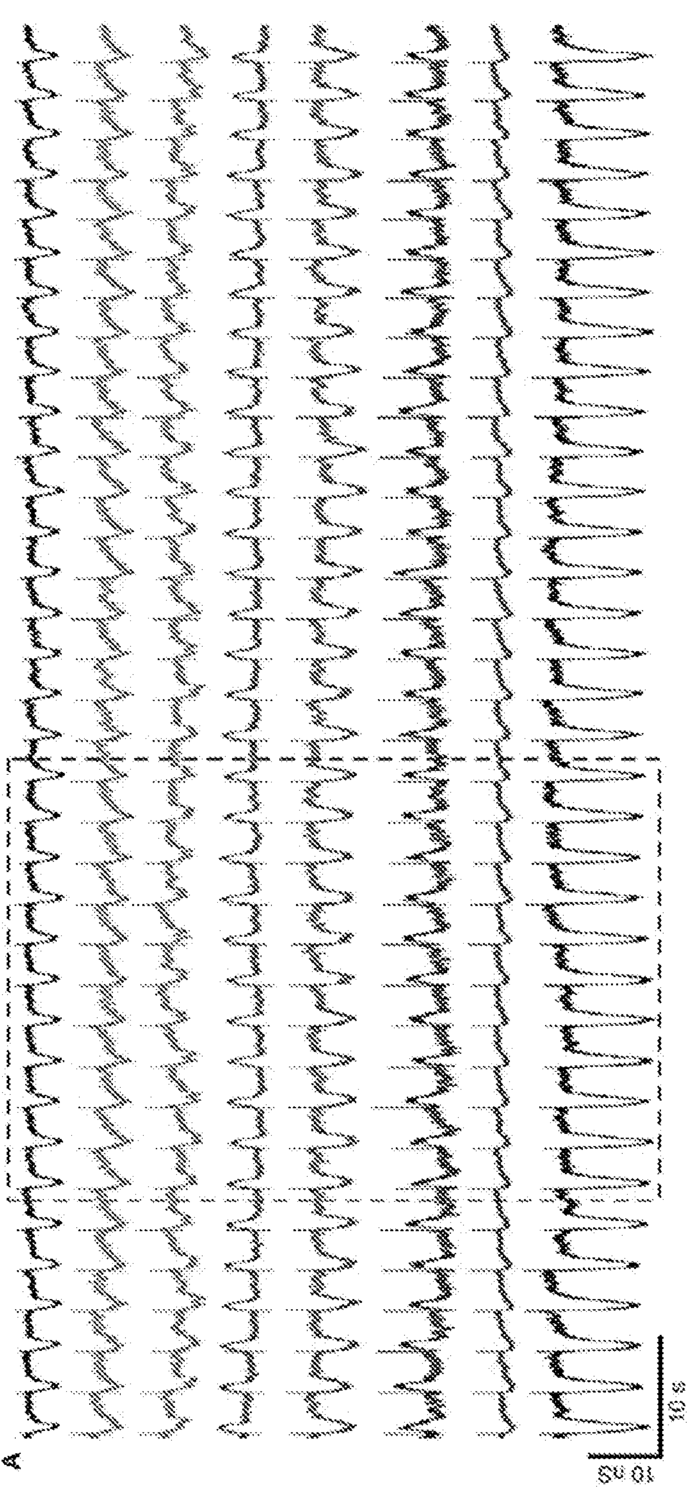
FIGS. 2A-2C show multi-channel recordings of AP and mechanical signals from exemplary biosensor devices of the present disclosure, where
Figure 2B:
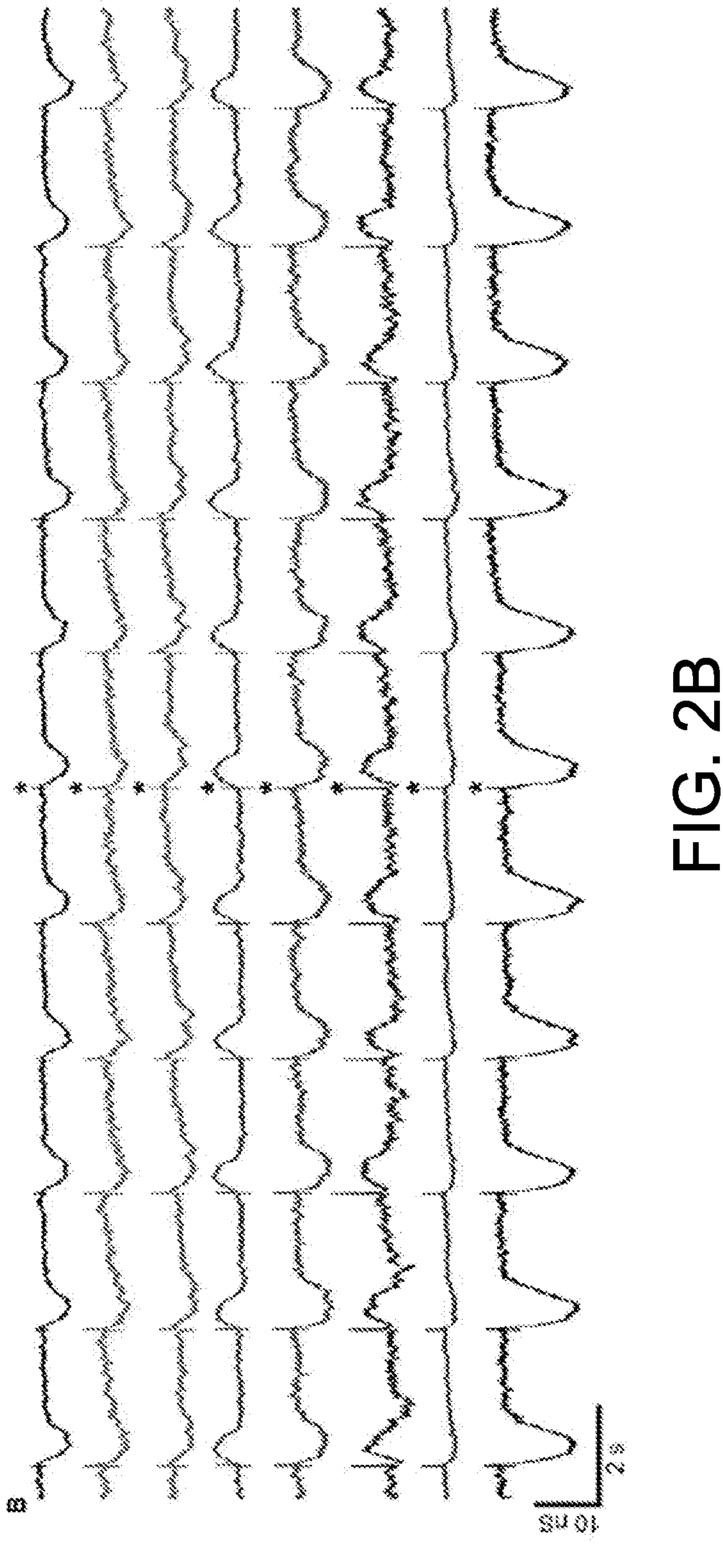
Figure 2C:
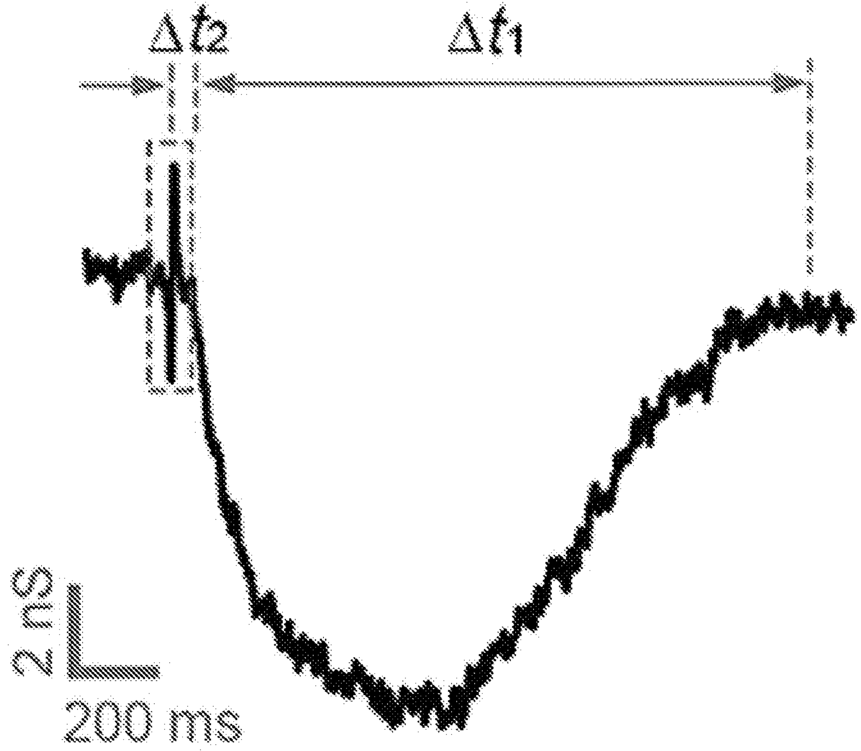
Figure 2D:
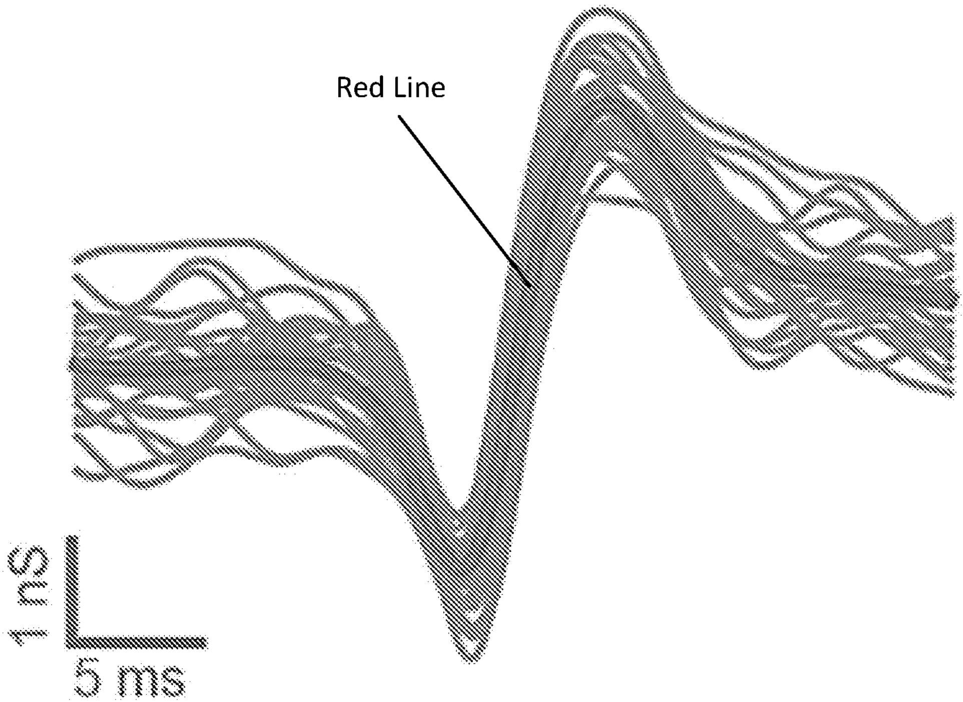
FIG. 2D shows superimposed AP signals.

These structural and functional properties demonstrate the potential in the semiconducting channel member 110 (e.g., nanotransistor) for multifunctional cellular probing. Human embryonic stem cell-derived cardiomyocytes (hESC-CMs), which are considered promising in vitro models of cardiac health and disease, were cultured on the device substrate. The scalable device arrays enabled multiplexed recordings from the monolayer cardiomyocytes forming synchronized contraction. Recordings from eight representative devices showed synchronized periodic signals, as shown in FIG. 2A. The signal frequency (~0.4 Hz) was consistent with typical contractile frequency in hESC-CMs. In each signal period, the broad peak was preceded by a sharp spike, where a star indicates the position of narrow spikes corresponding to AP, as illustrated in FIG. 2B. Correspondingly, FIG. 1C shows a zoomed-in signal in one period, where $\Delta t_1$ is the width of the broad signal and $\Delta t_2$ is the time delay between AP and the initiation of the broad signal. Analysis of the sharp spikes shows uniform potential waveforms with an average duration ~20 ms and converted amplitude of ~1.5 mV, as shown in FIG. 2D, characteristic of extracellular AP from hESC-CMs, where the red line represents the mean waveform. Recordings from human induced pluripotent stem cell-derived cardiomyocytes (hiPSC-CMs) showed similar results. The nanotransistor arrays also enabled real-time mapping of signal propagation across the tissue, revealing a conduction velocity ~4.5 cm/s consistent with values in in vitro hESC-CMs.

Figure 2E:
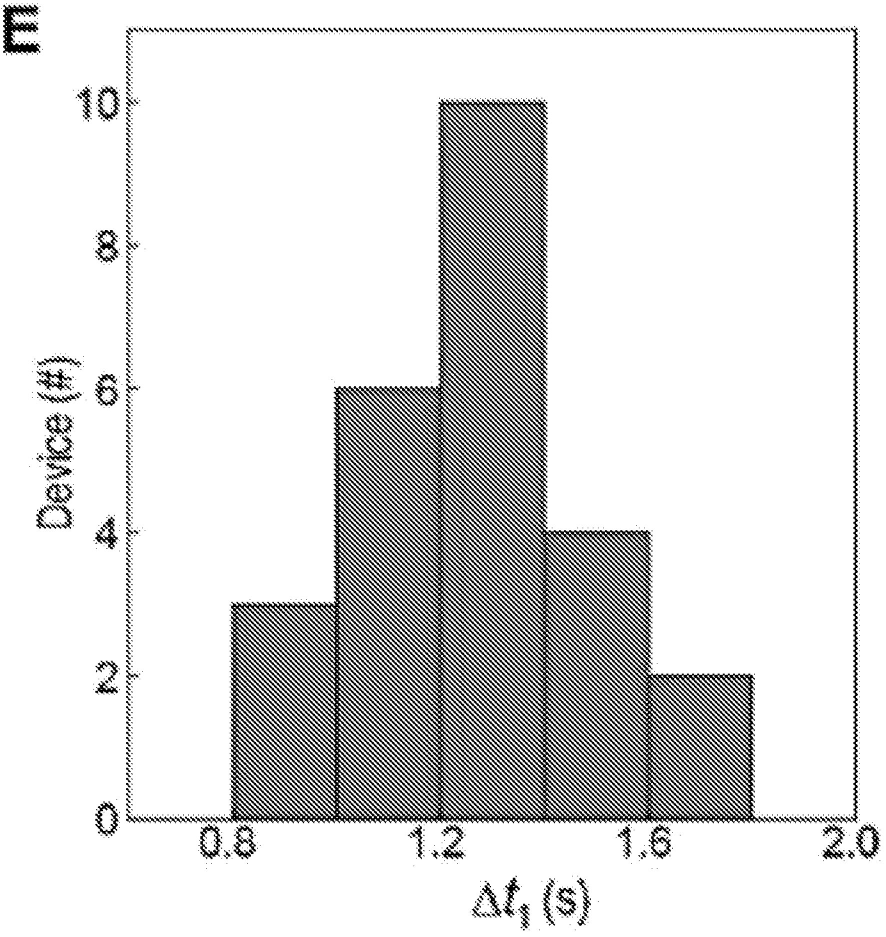
FIG. 2E shows a histogram of $\Delta t_1$ (N=25)
Figure 2F:
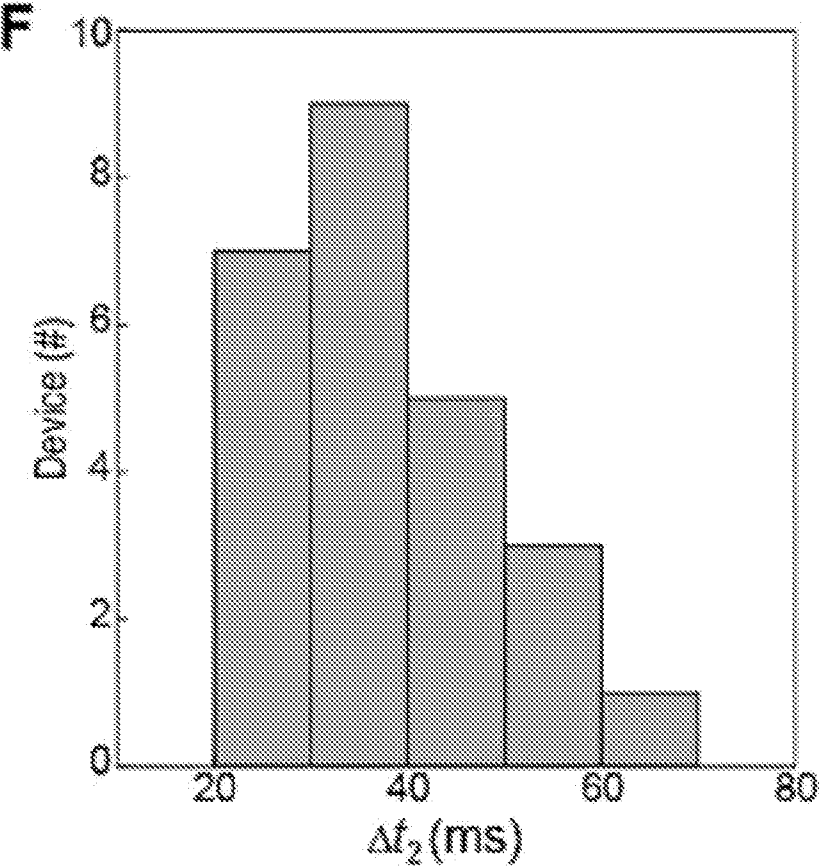
FIG. 2F shows a histogram of $\Delta t_2$ (N=25). $\Delta t_2$, $\Delta t_1$ are the time delay between AP and initiation of mechanical contraction, contractile duration as shown in FIG. 2C.

The broad peaks were analyzed to reveal the origin. First, the peak featured a slow rising edge (~600 ms), as depicted in FIG. 2C, which was distinct from the fast initiation of an intercellular AP. In fact, this signal was exclusively observed in the 3D nanotransistors here but not in previous electrical cellular sensors. Second, in FIG. 2E, the average duration of the signals ($\Delta t_1$~1.2±0.4 s) was consistent with the contractile time span in hESC-CMs. In particular, the evolution of the signal shape closely matched that of the contractile force. Third, in FIG. 2F, the time delay ($\Delta t_2$~35±10 ms) between the AP and signal initiation was consistent with the latency time of $Ca^{2+}$ release from the sarcoplasmic reticulum that activates contraction in cardiomyocytes. These analyses have indicated that the broad peaks arise from mechanical contraction in the cells.

Figure 3A:
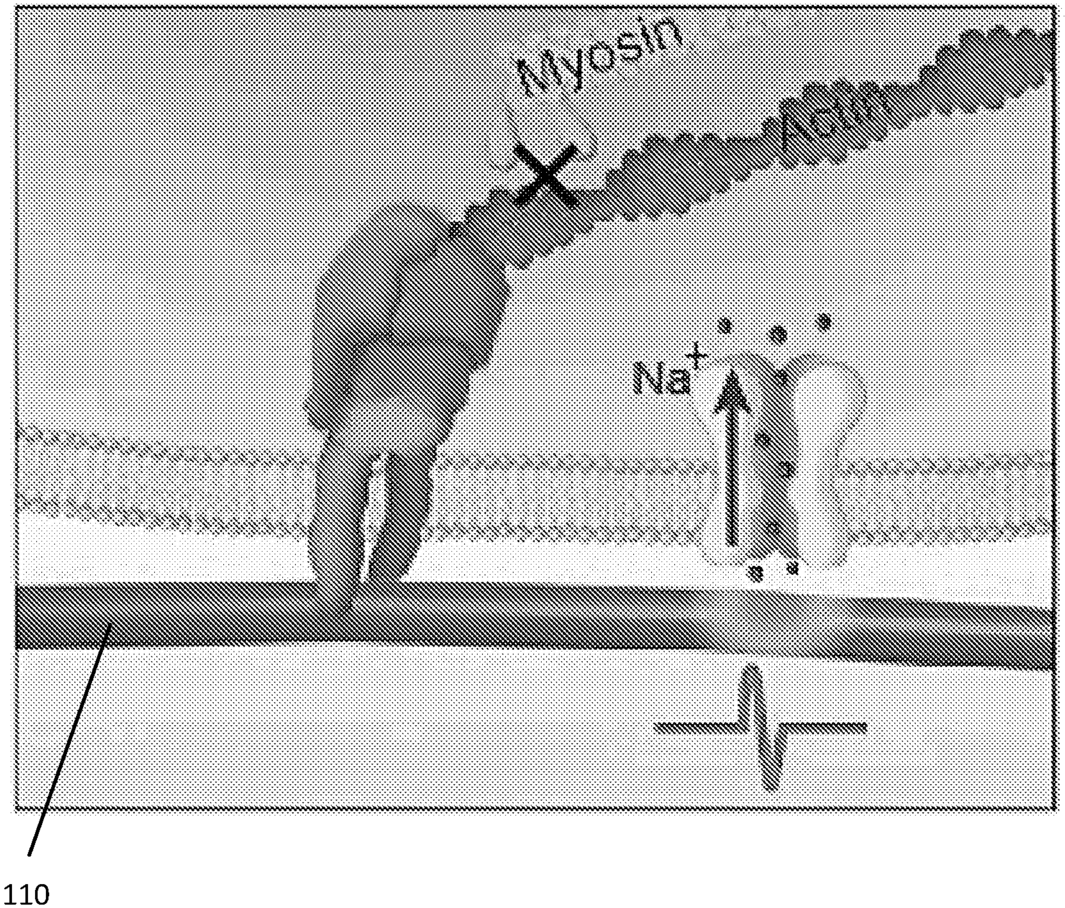
FIGS. 3A-3I show experimental results in detecting drug effects using an exemplary biosensor device of the present disclosure, where
Figure 3B:
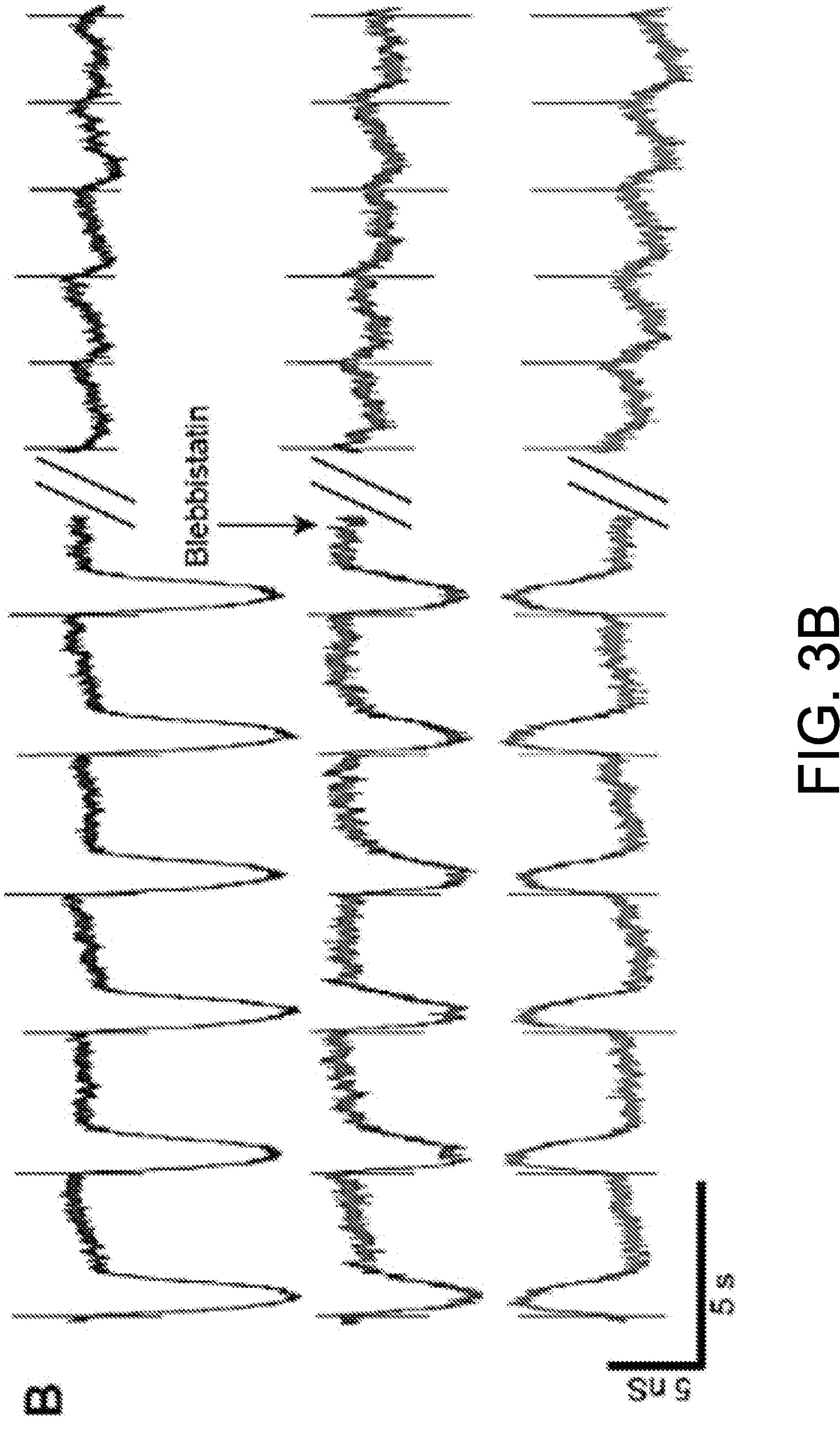
Figure 3C:
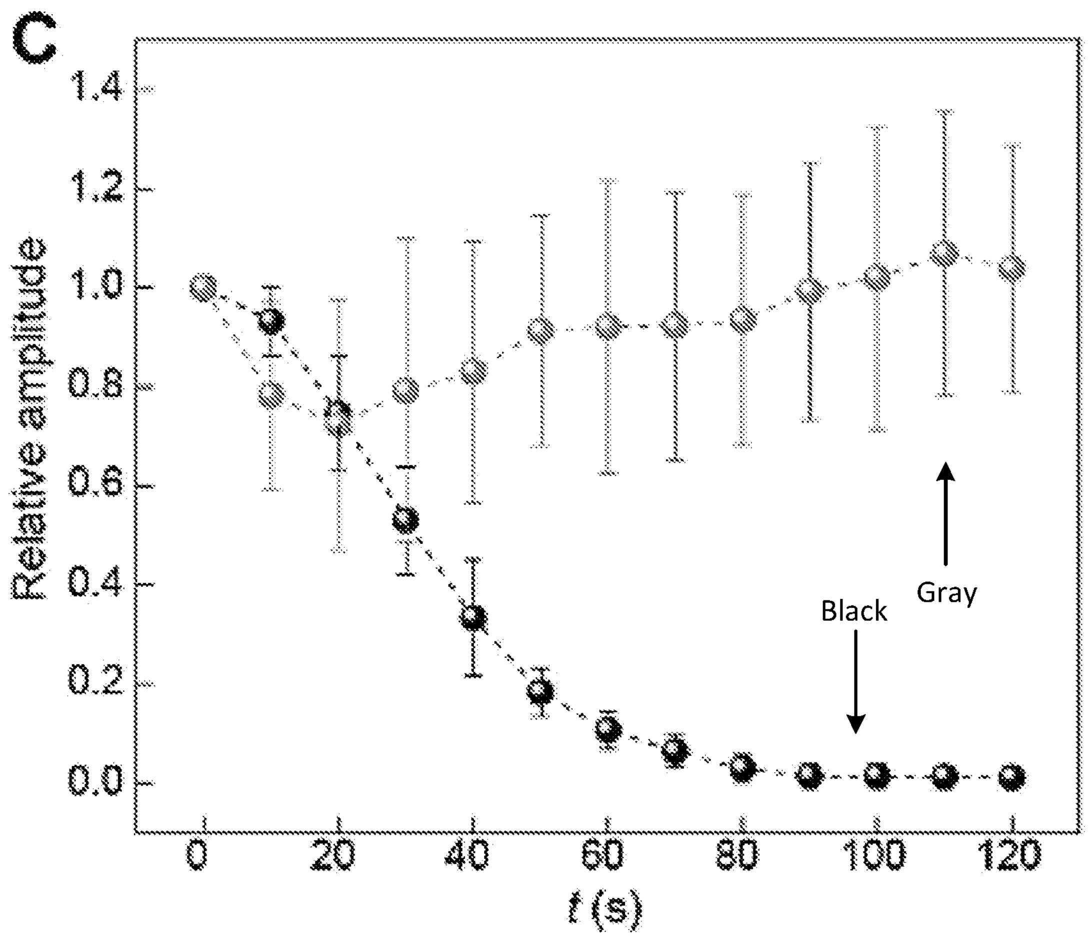

As part of experimental trials, drug tests were performed to further reveal the potential of implementing the sensors in pharmacological and pathological studies on cells. Blebbistatin, an inhibitor of myosin essential for motile machinery, was used to suppress cell contraction, as shown in FIG. 3A. The electrical recordings showed a substantial decrease in the amplitude of broad peaks after adding blebbistatin (20 μM), whereas the amplitude of AP maintained the similar level, as shown in FIGS. 3B and 3C. The maintenance of AP indicated unaffected electrophysiological activity in cells, revealing that the signal depression was exclusively related to suppression of cell contraction. Washing out blebbistatin restored the broad peaks. Notably, the evolution in signal amplitude, as shown in FIG. 3C, matched the decay profile of sarcomere shortening in cardiomyocytes perfused with blebbistatin, showing that the sensor can closely track drug effect in developmental stages.

Figure 3D:
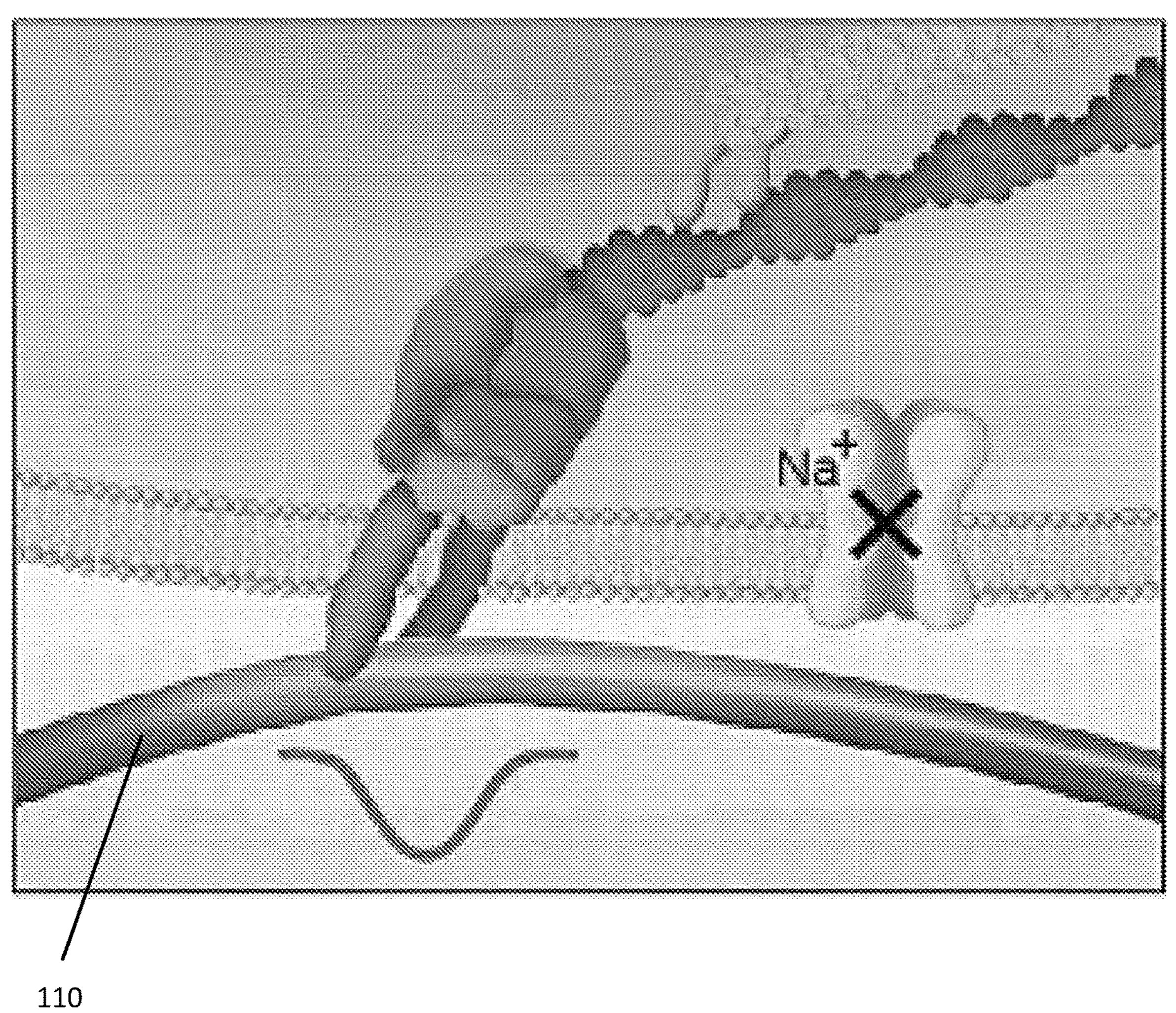
Figure 3E:
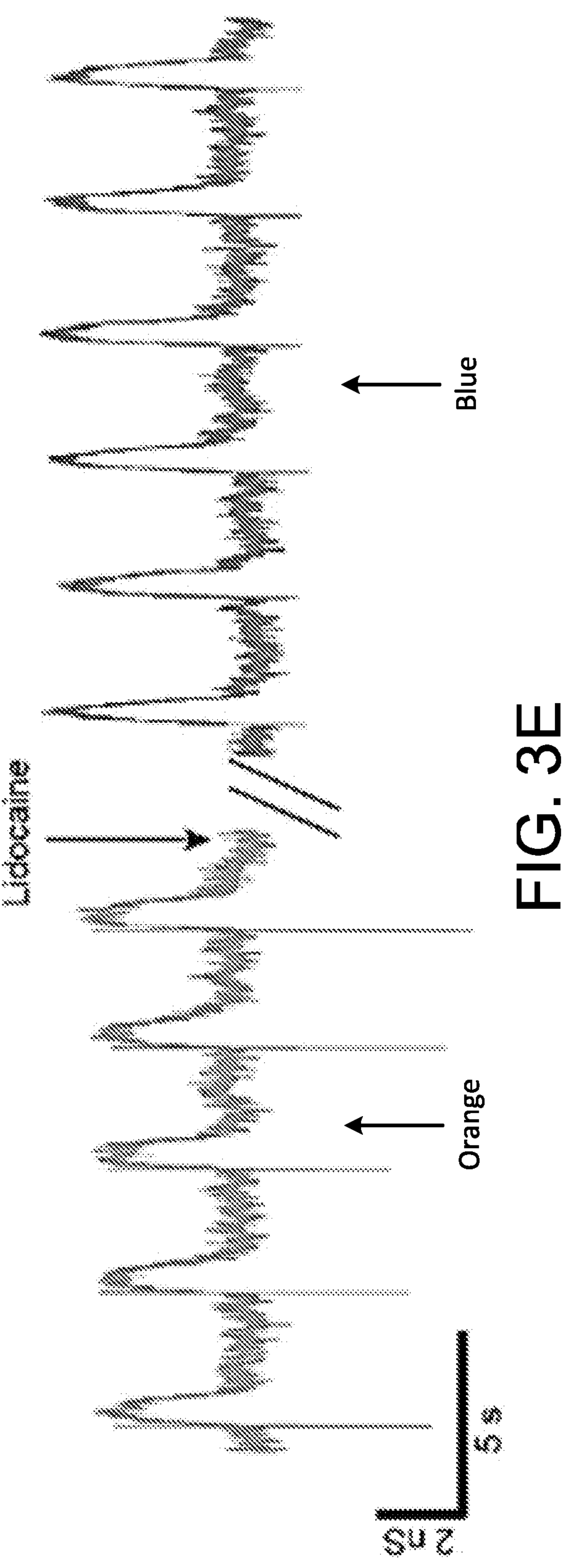
Figure 3F:
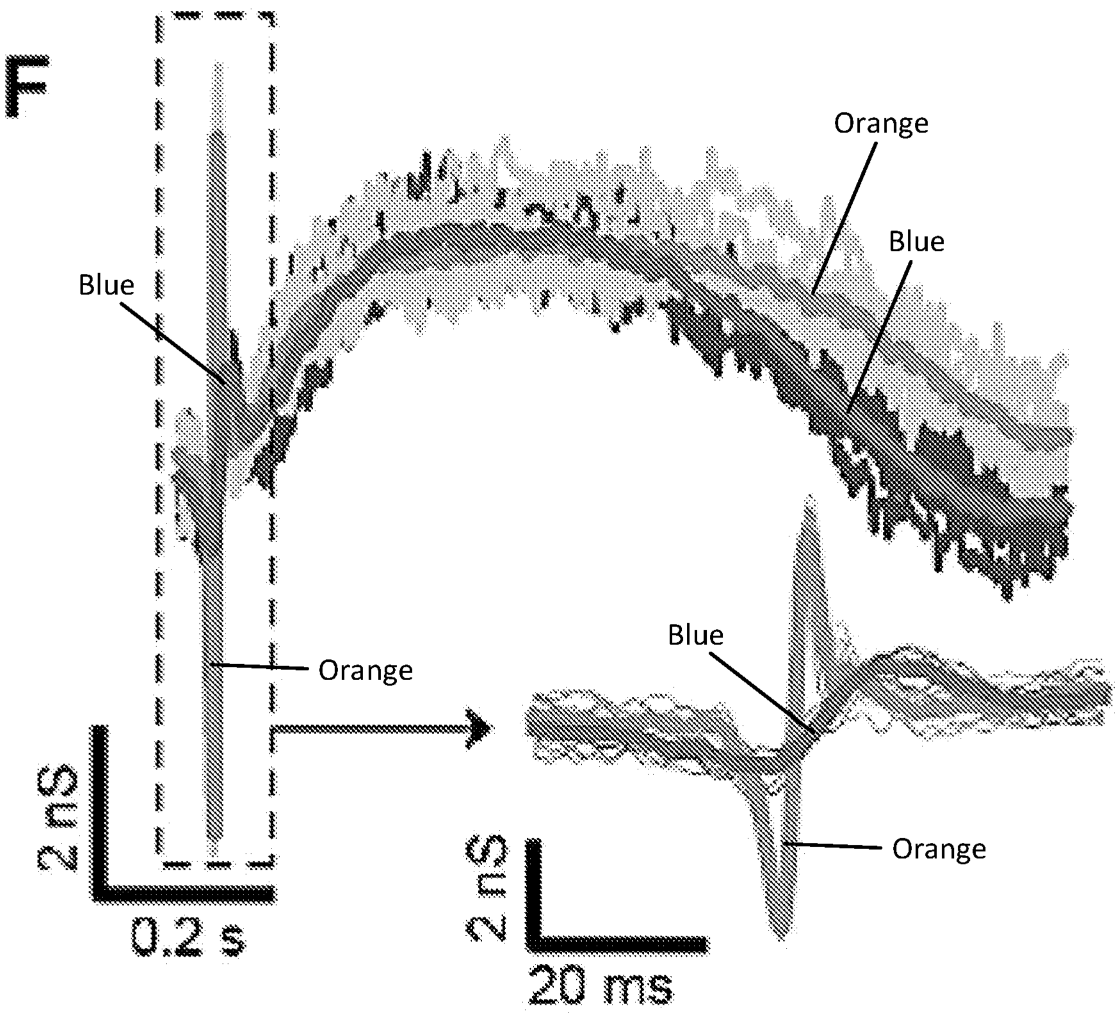

Conversely, lidocaine, a Na+ channel blocker, was added to suppress Na+ influx which contributes mostly to extracellular AP, as shown in FIG. 3D. The electrical recording, in FIG. 3E, showed a prominent suppression in AP but no obvious effect on the mechanical signal after the introduction of lidocaine (20 μM). The sensor revealed further details of the AP evolution, in which the amplitude reduced from ~10 nS to ~2 nS and the duration increased from ~19 ms to ~40 ms, as shown in FIG. 3F. The observed trends were consistent with the drug mechanism in both reducing and slowing Na+ influx.

Figure 3G:
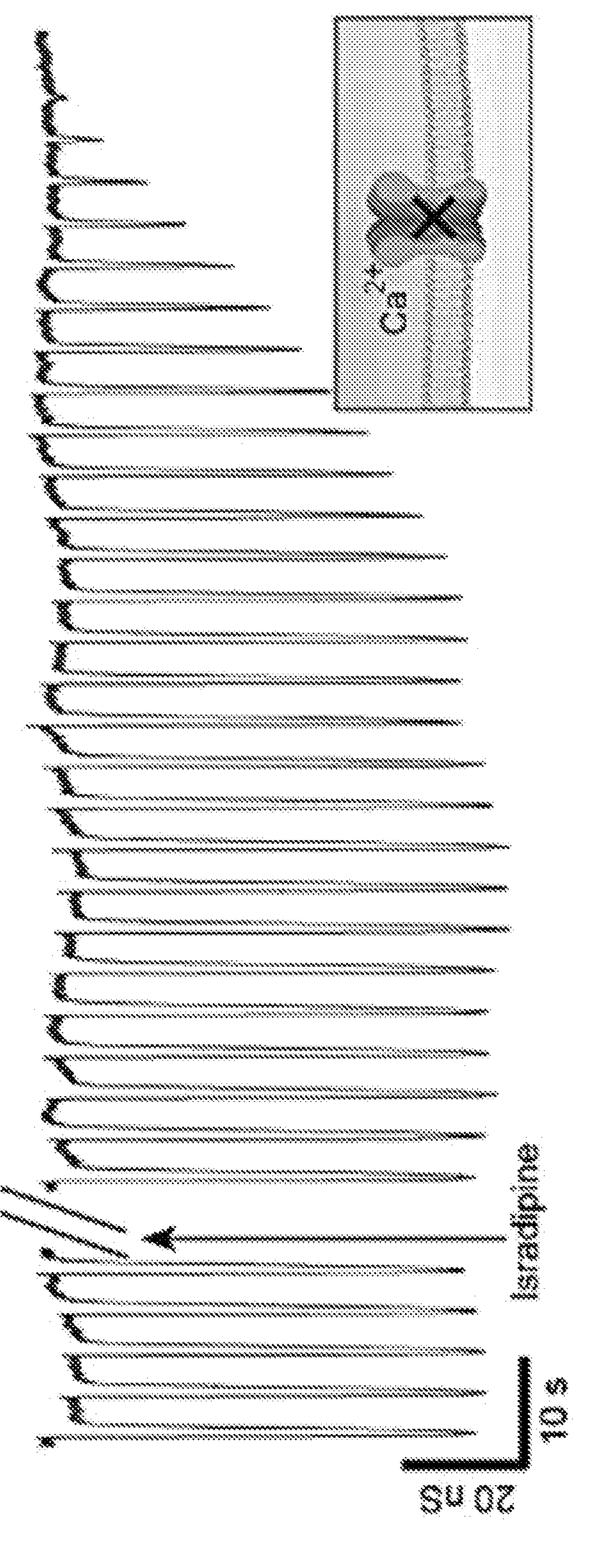
Figure 3H:
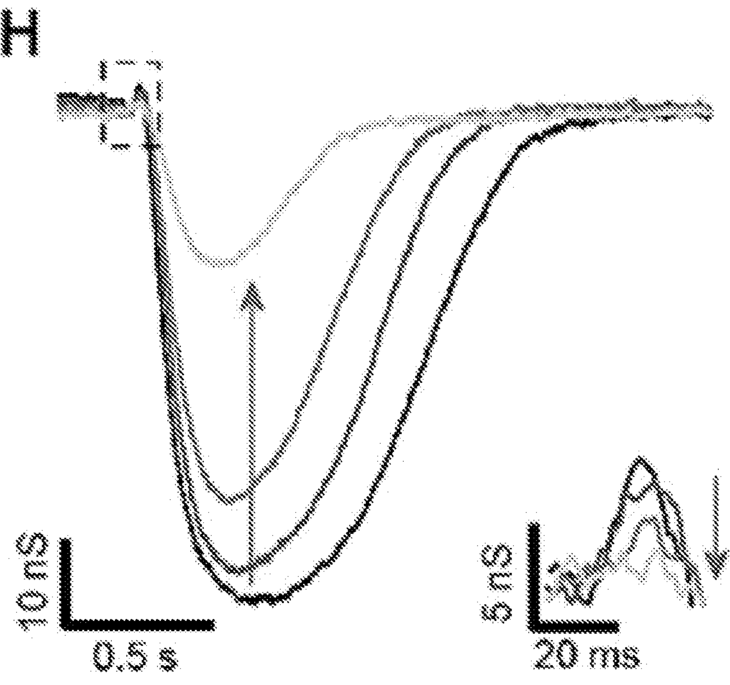
Figure 3I:
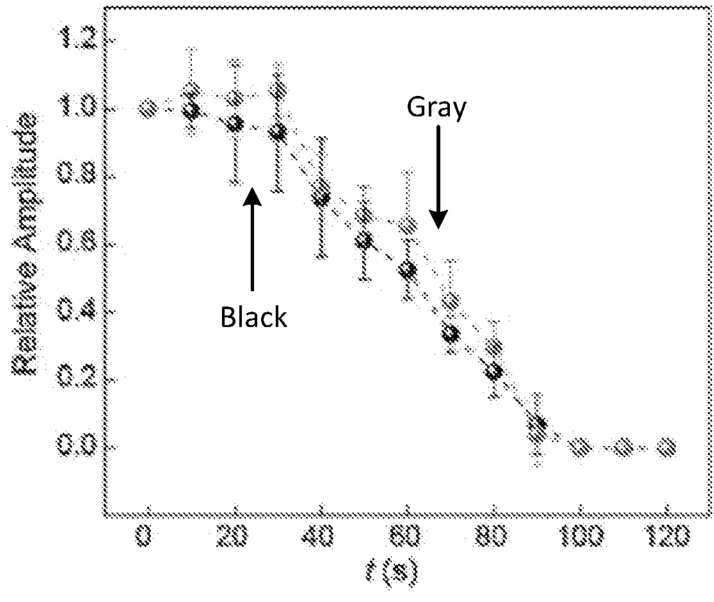

A $Ca^{2+}$ dysfunctional model was also built by treating the cardiomyocytes with isradipine, a $Ca^{2+}$ channel blocker used for treating a wide variety of cardiovascular disorders, as shown in FIG. 3G and its inset. The treatment of isradipine (20 nM) led to the apparent suppression of a mechanical signal in about 100 seconds, as illustrated by FIGS. 3G and 3H, which was consistent with the mechanism of $Ca^{2+}$-activated contraction. Unlike the effect from blebbistatin, the exemplary biosensor revealed a concurrent decrease in AP, as depicted in FIGS. 3H and 3I, which was consistent with the mechanism of a concurrent suppression of Na+-channel current by isradipine. Washing out isradipine restored both signals, showing the robustness in the sensor for tracking correlated E-C dynamics across different stages. The isradipine effect, see FIG. 3I, can be readily differentiated from blebbistatin effect, see FIG. 3C, and the lidocaine effect, see FIG. 3F, by the exemplary biosensor with the E-C dynamics tracked simultaneously.

An additional drug test involving the treatment of E-4031, a $K^+$ channel blocker, yielded fluctuations in contractile frequency and amplitude captured by the sensor, which was consistent with traits in $K^+$ blocker-induced arrhythmia behavior. The treatment of norepinephrine, on the other hand, yielded increased contractile frequency and an alteration of the conduction pathway captured by the exemplary biosensor. These drug tests have shown that an exemplary 3D nanotransistor biosensor can capture the details of electrical and mechanical activities throughout different cell stages. The correlated information offers the unique advantage in differentiating cell states and drug effects, which otherwise may not be achieved through a single-parameter measurement of mechanical or electrical response. As a result, it constitutes a promising candidate for assembling sensing platforms for cell-mechanism studies and drug models.

Electrical recording of mechanical properties in cardiac tissue offers additional advantages for constructing organs-on-chips. The 3D nanotransistor biosensor can achieve cellular resolution beyond the tissue resolution from previous sensors. The recordings in mechanical signals were therefore investigated in the present disclosure. An exemplary biosensor of the present disclosure detected both positive and negative signals, as shown in FIG. 2A, with the majority (~73%) being negative. To better understand the results, simulations were performed to study the mechanical coupling between a cell and the biosensor device, as shown in FIG. 4A.

Via computer modeling of the cell-sensor mechanical coupling, cardiomyocyte was simulated by a 10×10×40 $\mu m^3$ (H×W×L) box, with the contractile direction along the y-axis (L) and symmetric about the central plane y=0. For symmetry, it was assumed that the sensor was in the left half of the cell of 10×10×20 $\mu m^3$, with the boundary condition that the cell plane at y=0 could not move in y direction (but could slide in the x-z plane). At the extracellular interface, the cell model was excavated at the device region with the surface of the excavation following the geometry of the sensor, such that the sensor was in direct contact with cell surface (cell membrane). The cell consists of passive and contractile components as introduced previously. Linear elastic model was used for both components. To simulate the myofibril coverage in cardiomyocyte, the contractile component consists of 25 (5×5) cylindrical beam elements (r=0.5 μm, E=67 kPa) distributed along the cell totaling ~20% of the cell body, and the rest of the box (~80%) was filled with passive component (E=13.5 kPa). Also, a Poisson's ratio of 0.48 (incompressible) was used for both components. The cell contraction was achieved through thermal contraction in the beam elements by reducing the temperature, which was to mimic sarcomere shortening caused by contraction in myofibrils. A contractile ratio of 10% in the beam elements was used, corresponding to typical value in cardiomyocytes shortening. Different contractile directions were obtained by rotating the sensor from 0° to 90° in increments of 15°. Finite-element mesh density of 0.1-1 μm was used, with the convergence confirmed by a mesh refinement. As additional boundary conditions, no sliding was allowed at the bottom interface (cell-substrate and cell-nanowire interface). Also, the front and back surfaces of the cell (x=10, x=0) were allowed to slide in y-z plane but not in x direction (a frictionless-wall condition).

Figure 4A:
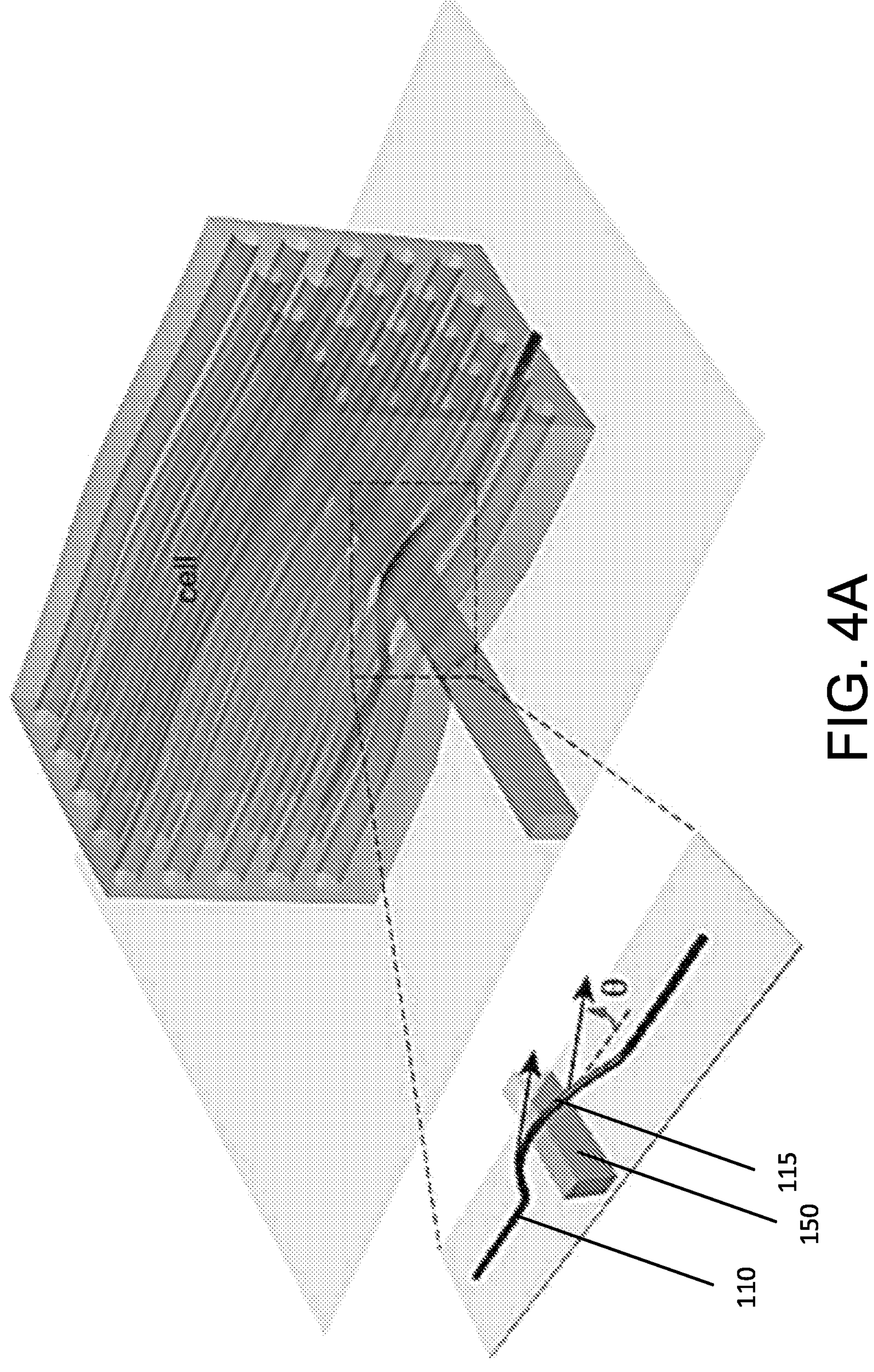
FIGS. 4A-4F illustrate the correlation between a mechanical sensing signal and cellular motion, where FIG. 4A demonstrates modeling of cell-sensor coupling.
Figure 4B:
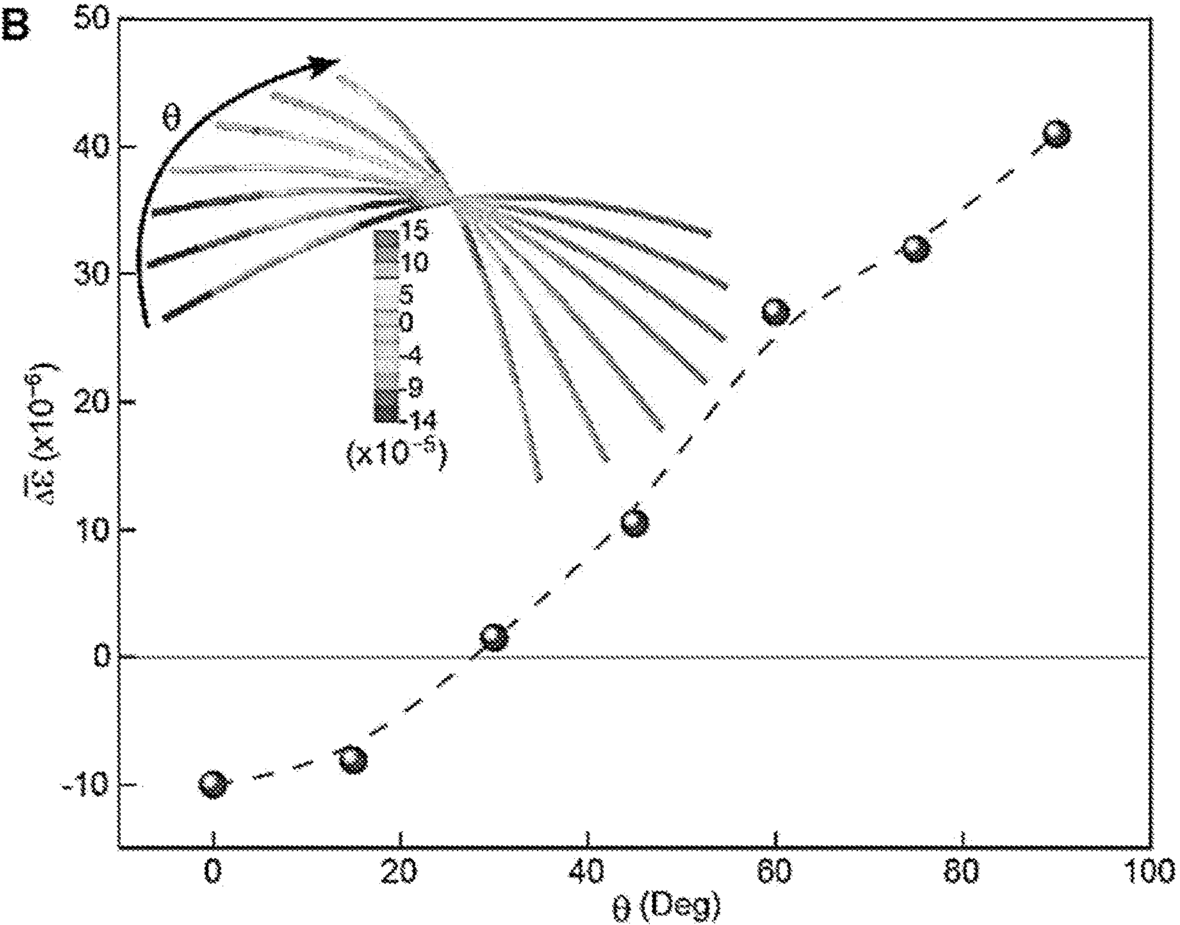

As the biosensor nanotransistor device was much smaller than the cell, it was assumed to experience uniform local motion dominated by an in-plane component characterized by an angle θ with respect to the nanowire axis, as shown in FIG. 4A. The cell contractile direction is characterized by an angle θ with respect to the nanowire axis due to structural symmetry, $0° \leq \theta \leq 90°$. Thus, the simulations show that the net strain in the nanowire transits from compressive to tensile when θ increases from 0° to 90°, as shown in FIG. 4B, with the threshold angle of ~29°. If we consider a random distribution, ~68% of the devices are expected to experience tensile strain or a negative sensing signal, which is consistent with the experimental observation. Specifically, the strain distribution yields expected average values of $2.2\times10^{-5}$ and $-9.0\times10^{-6}$ for tensile and compressive strain, respectively, as shown in FIG. 4B. For an average gauge factor of $\sim7.6\times10^{2}$, these values correspond to expected average conductance changes of −1.67% and 0.68%, respectively. These values are also close to experimental values of −1.67% and 0.48%, respectively.

Figure 4C:
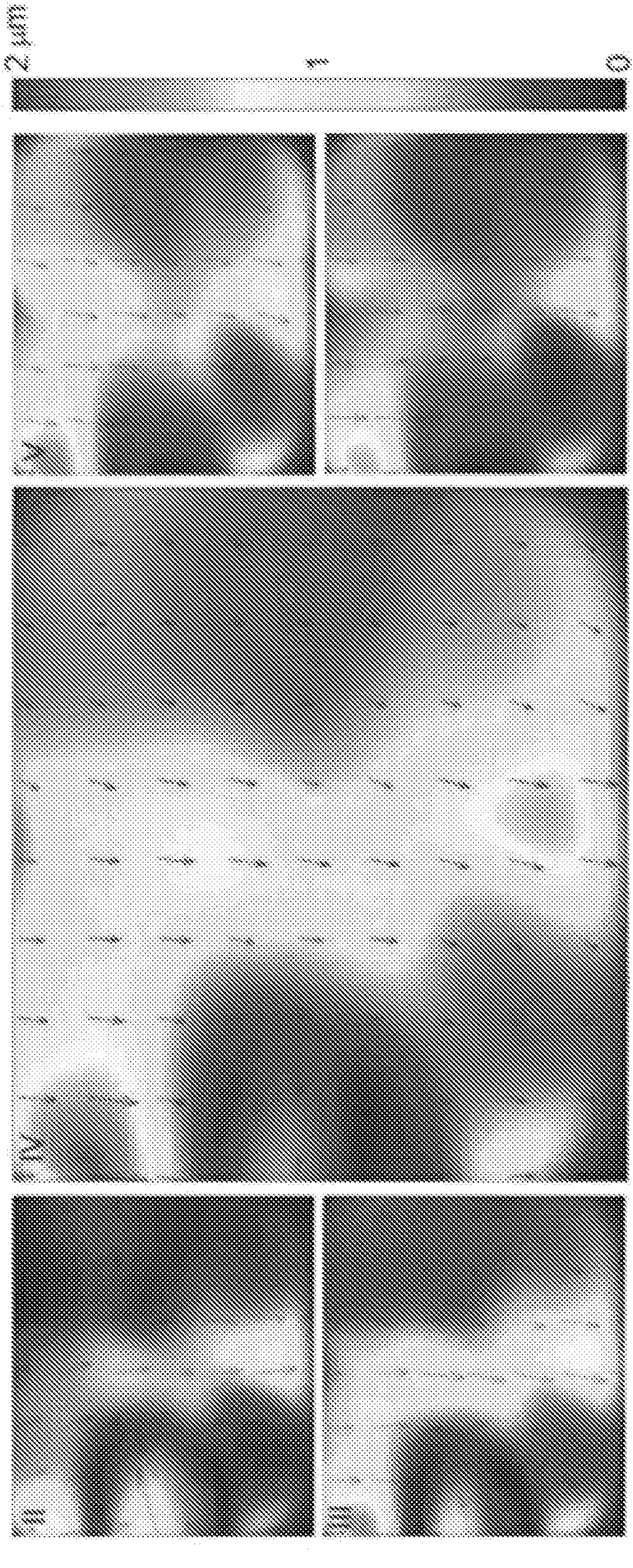

The correlation between the sensing signal and mechanical activity was investigated by combining the electrical recording with optical imaging. Cellular motion was revealed by analyzing consecutive image frames captured during a contractile cycle, as shown in FIG. 4C. A clear trend from contraction (II-IV) to relaxation (IV-VI) was shown. And, in FIG. 4D, the data sets ($\overline{D}$, $\overline{\theta}$) correspond to frames in FIG. 4C, with the 4th set (highlighted by gray bar) corresponding to frame IV. It is noted that the $\overline{\theta}$ value is insignificant at resting states (frames I and VII) and hence not plotted. The dashed line indicates the simulated threshold angle of 29°.

Figure 4D:
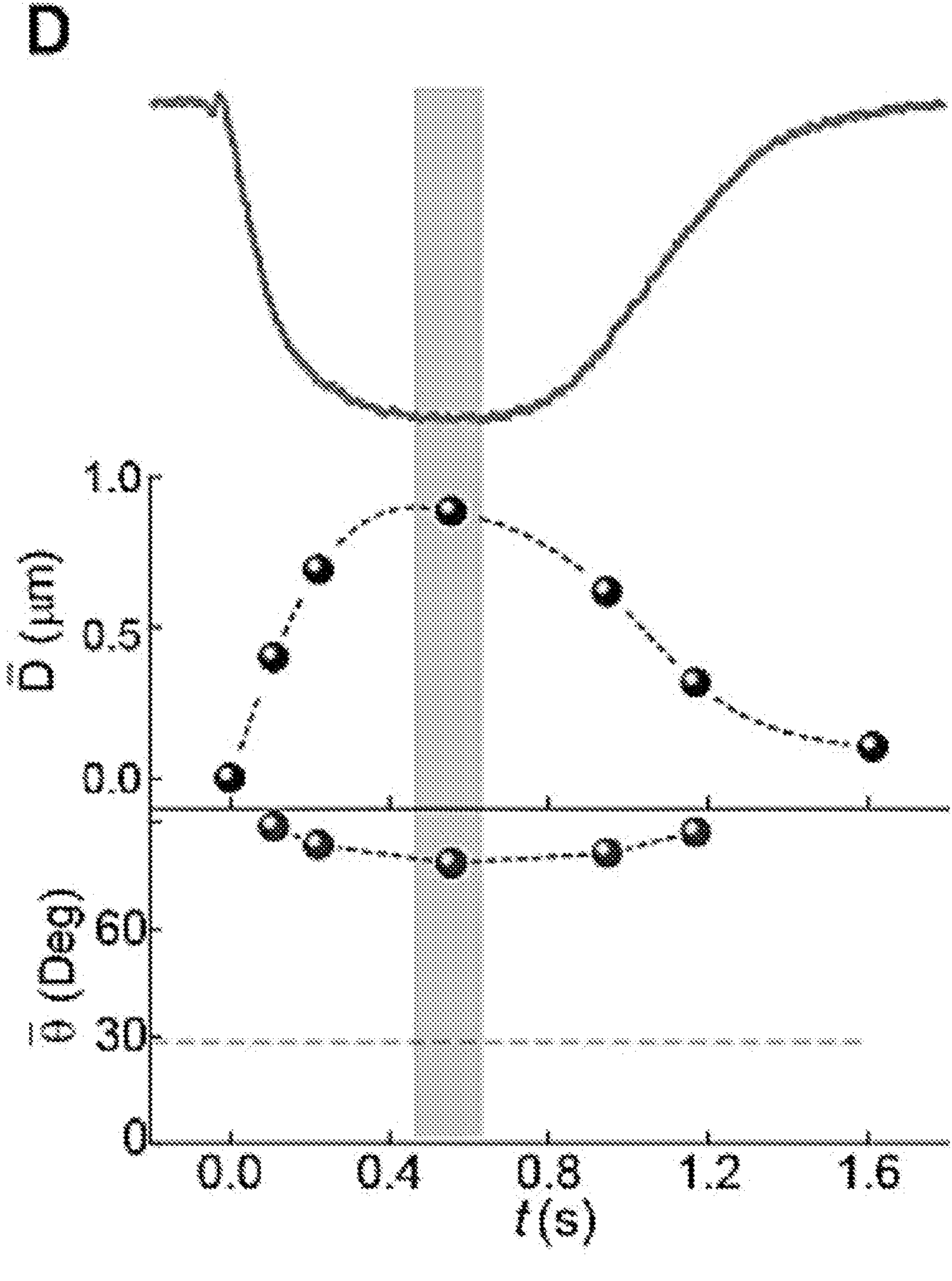
Figure 4E:
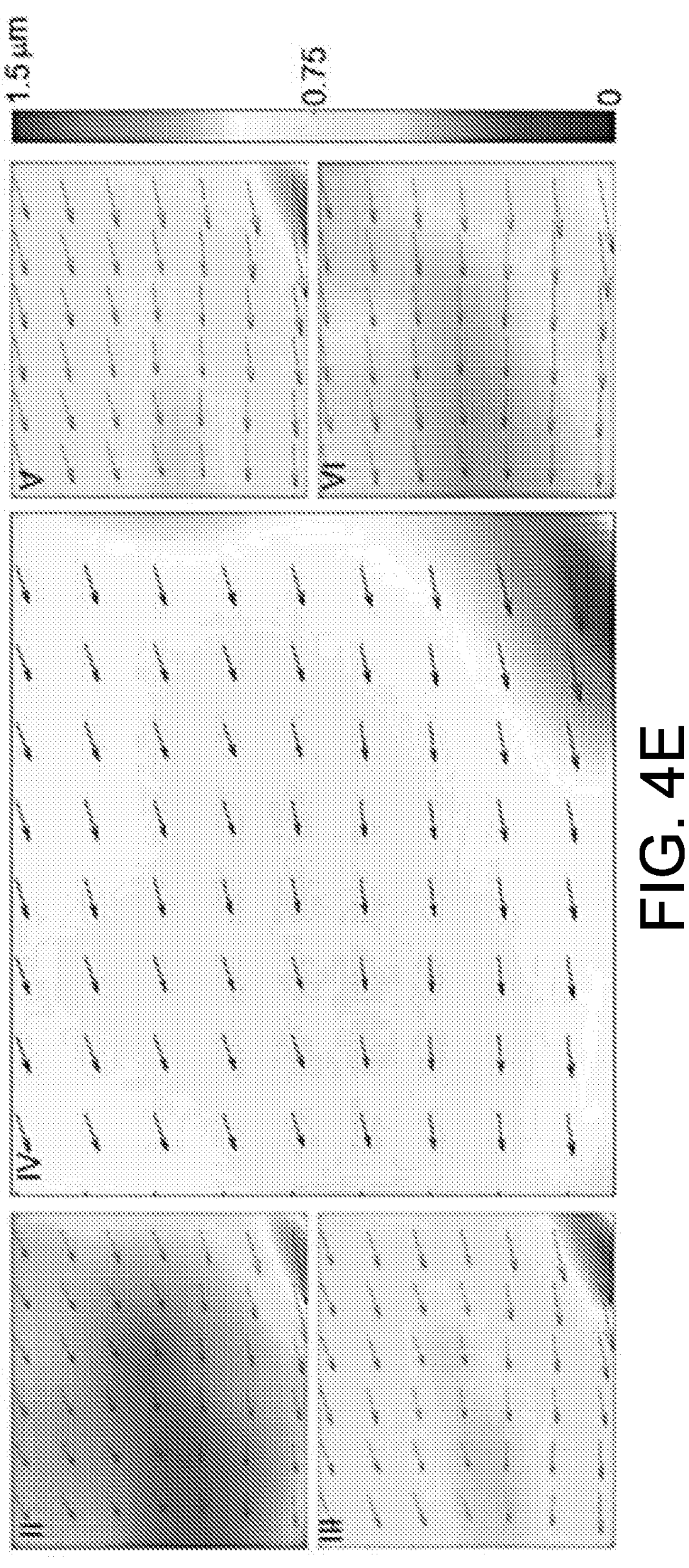
Figure 4F:
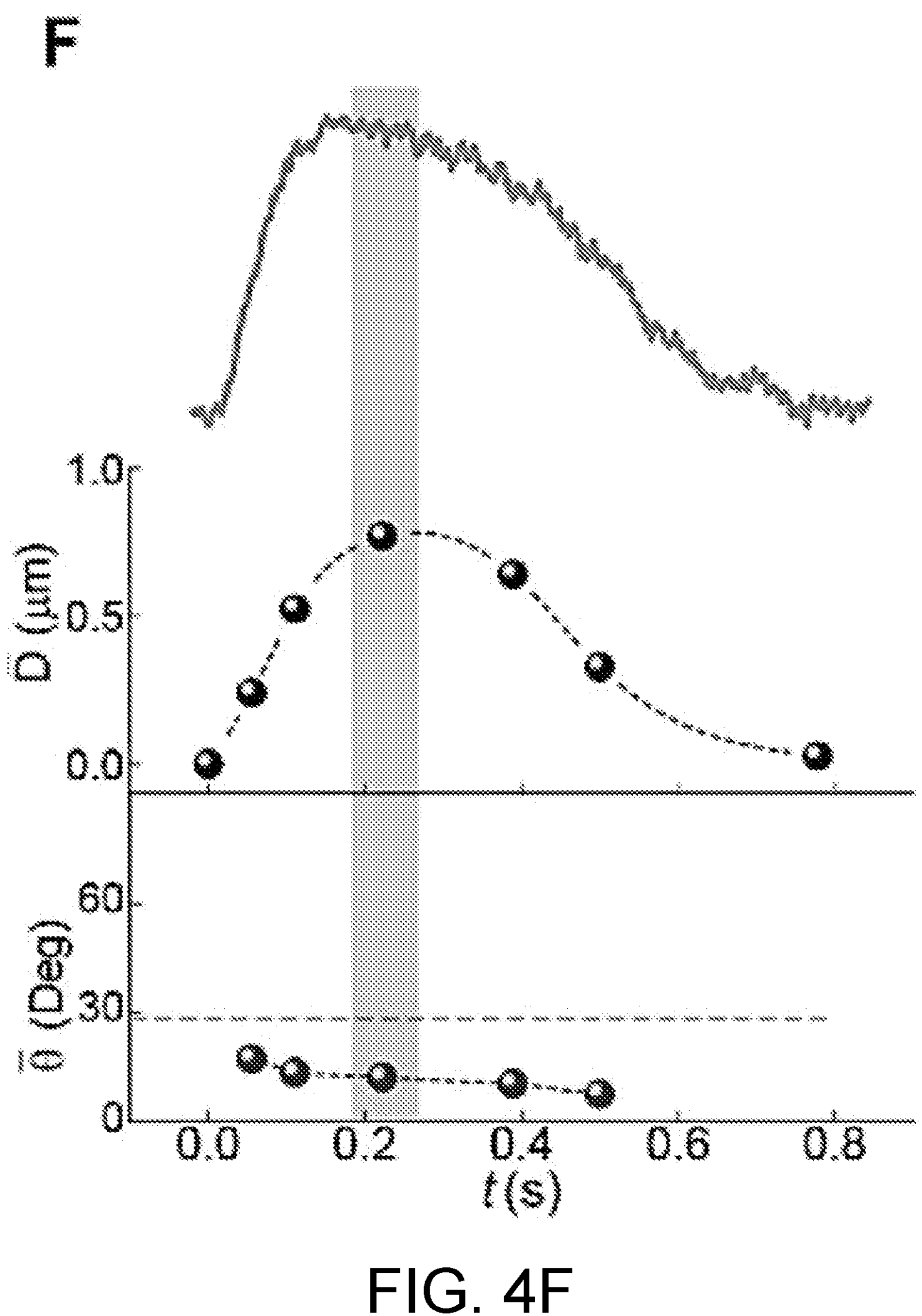

Specifically, the average displacement ($\overline{D}$) of cellular motion at the device region, as show in the middle panel or portion of FIG. 4D, was compared with the electrical recording (top panel), showing a close match between their evolutions. In particular, the slight asymmetry in the contractile dynamics featuring a slower relaxation was clearly captured in the electrical recording (e.g., $t_{rising}$: $t_{falling}$=0.6: 1.0 s). Meanwhile, the local vectors of cellular motion in each frame were also analyzed (as demonstrated by the arrows in FIG. 4C). The average angle ($\overline{\theta}$) of the vectors with respect to the nanowire axis was above 75° throughout the contractile cycle, as shown by the bottom panel of FIG. 4D. The $\overline{\theta}$, above the threshold value of 29° from simulation (FIG. 4B), was expected to induce a net tensile strain in the nanowire or a conductance decrease, which was consistent with the electrical recording, as shown by the top panel of FIG. 4D. Analyses in cell contraction (FIG. 4E) producing a positive sensing signal (top panel, FIG. 4F) showed consistently a close match between the signal amplitude and cellular displacement (middle panel, FIG. 4F). However, the average 0 was below the threshold value of 29° (bottom panel, FIG. 4F), which is consistent with the expected compressive strain or a conductance increase. Analyses from all sampled devices showed results consistent with computer simulations.

These results show that the 3D nanotransistor can differentiate cellular motion, which was not possible in planar sensors, providing additional information for cell studies. Multiple sensors of different orientations can be combined to reveal further details of the contractile vector, transcending a mere amplitude (i.e., scalar) detection in current electrical platforms. In particular, since the nanotransistor is much smaller than the cell, a 'pixel' containing multiple sensors can still achieve or approach cellular resolution.

Figures 5A, 5B:
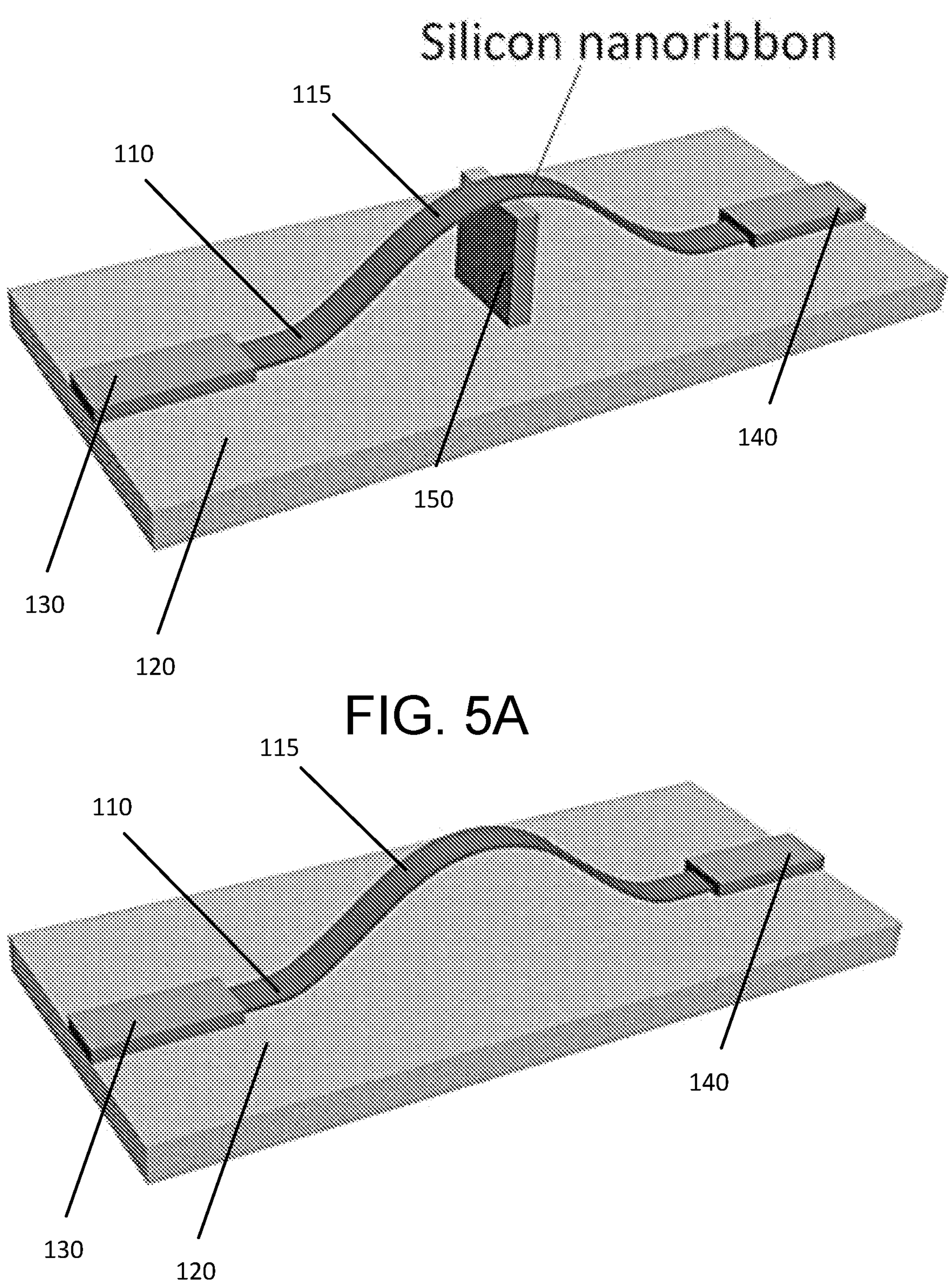
FIGS. 5A-5B show alternative embodiments of a biosensor, where the semiconducting channel member comprises a silicon nanoribbon in accordance with the present disclosure.
Figure 6A:
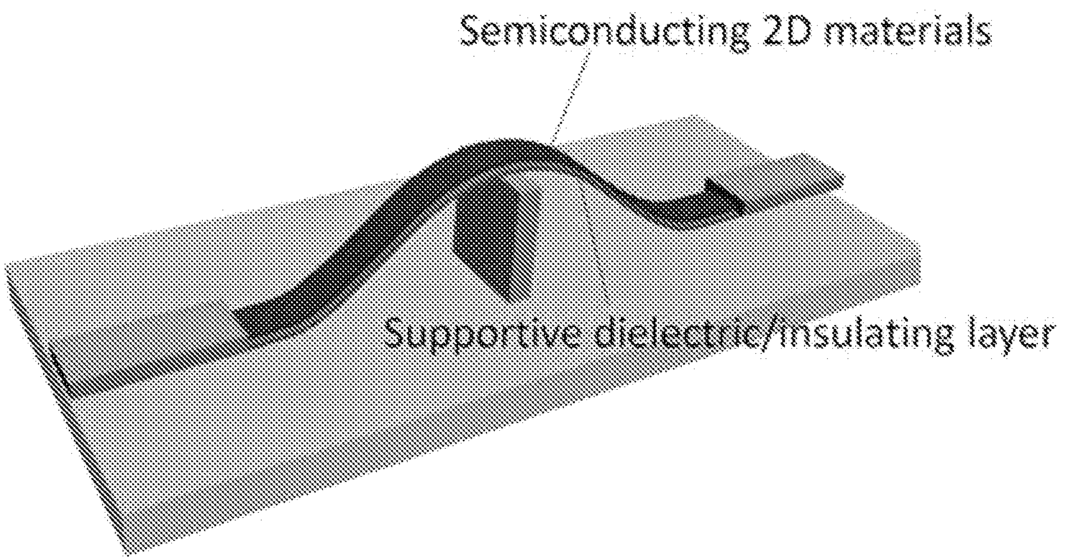
FIGS. 6A-6B show alternative embodiments of a biosensor, where the semiconducting channel member comprises semiconducting 2D materials having a supportive dielectric/insulating layer in accordance with the present disclosure.
Figure 6B:
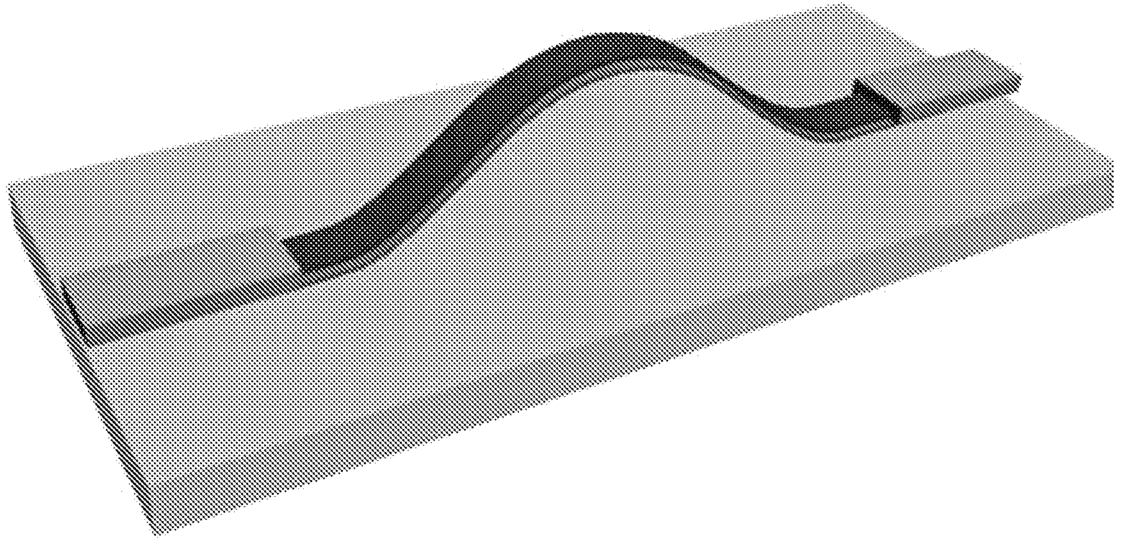

Referring now to FIGS. 5A and 5B, alternative embodiments of a biosensor are provided, where the semiconducting channel member comprises a silicon nanoribbon. Thus, the semiconducting channel member may be made from a Si nanoribbon (e.g., etched from Si wafer) instead of synthetic Si nanowire, in various embodiments, which can lead to industrial-compatible fabrication and integration, achieving high device yield and uniformity desirable for commercial biochips. In FIG. 5A, the convex protruding channel 115 is supported with a mechanical support structure 150 and in FIG. 5B, the convex protruding channel 115 is self-supporting (and does not rely on a mechanical support structure). In other alternative embodiments, the semiconducting channel member can be replaced with other 2D semiconducting materials (e.g., graphene, $MoS_2$, etc.) and the convex protruding channel can include a supportive dielectric/insulating layer, as shown in FIG. 6A. Correspondingly, the convex protruding channel 115 can be additionally supported with a mechanical support structure 150, as shown in FIG. 6A, or can be self-supporting (and does not rely on a mechanical support structure), as shown in FIG. 6B.

Figure 7A:
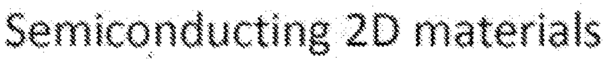
FIGS. 7A-7B show alternative embodiments of a biosensor, where the semiconducting channel member comprises semiconducting 2D materials having a top layer for detecting bioelectrical signal and a bottom layer for detecting biomechanical signal in accordance with the present disclosure.
Figure 7A:
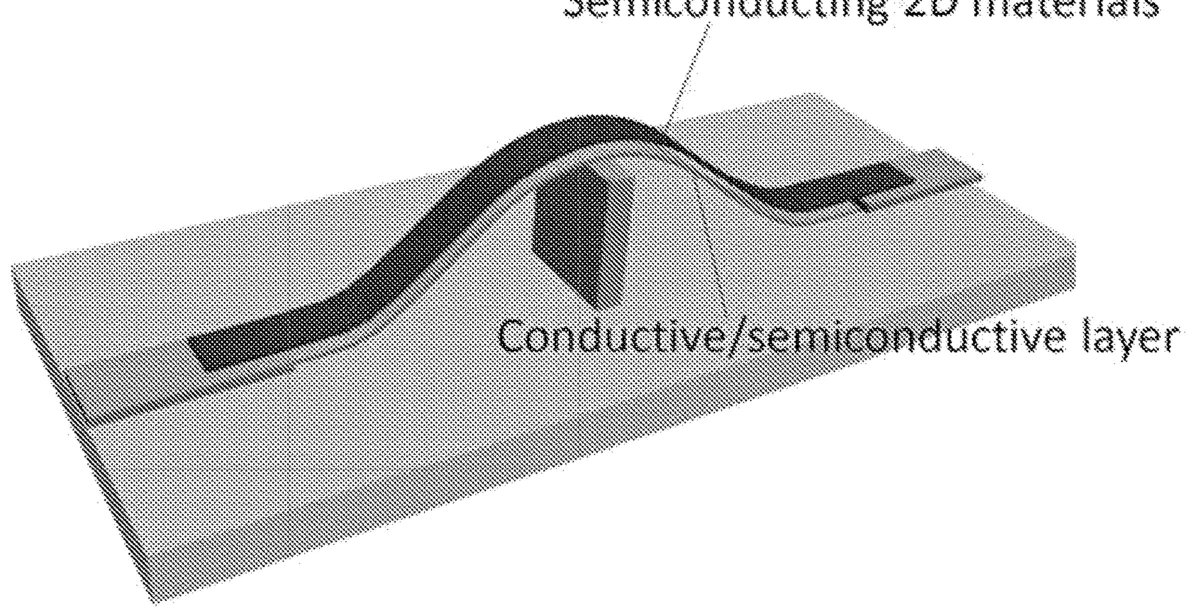
Figure 7B:
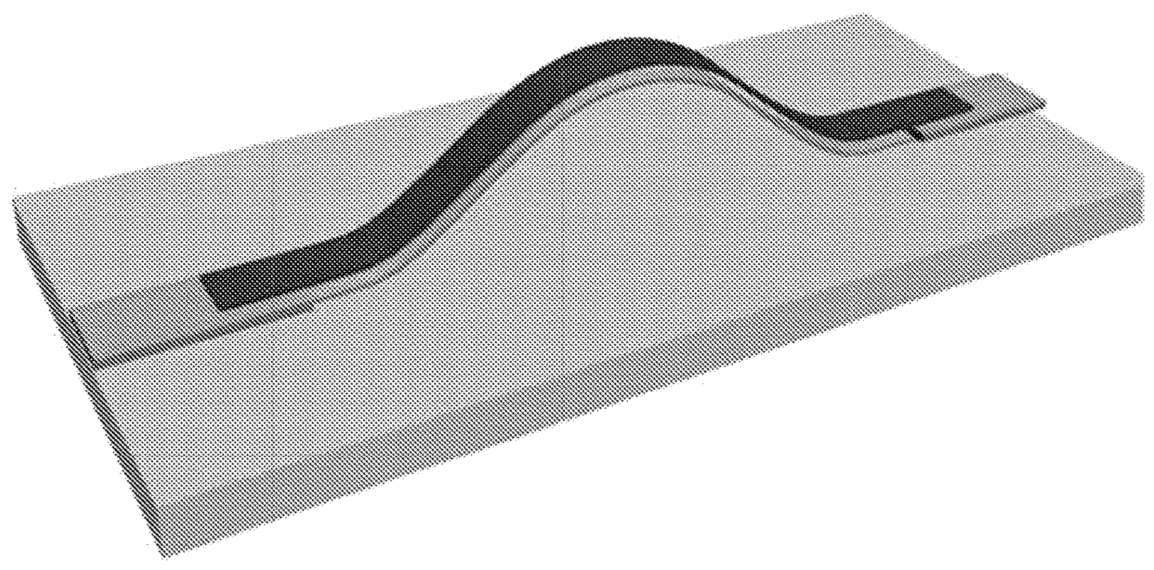

While the biosensor devices of FIGS. 5A and 5B rely on a single ribbon layer for the detection of bioelectrical and biomechanical signals, an extension is to use two stacking layers for detection purposes with the top layer detecting bioelectrical signal and the bottom layer detecting biomechanical signal, as shown in FIGS. 7A and 7B. In various embodiments, each of the stack of nanoribbons can be different from silicon. For example, the top layer can be any semiconducting materials (silicon, graphene, $MoS_2$, and other 2D/thin film semiconductors). Subsequent layers can be any semiconducting/metallic materials. This type of design can lead to a broader material choice for enhanced signal detection (e.g., with each layer optimized for the targeted signal). Here, the convex protruding channel 115 can be either supported by a mechanical support structure, as shown in FIG. 7A, or can be self-supported, as shown in FIG. 7B.

Figure 8:
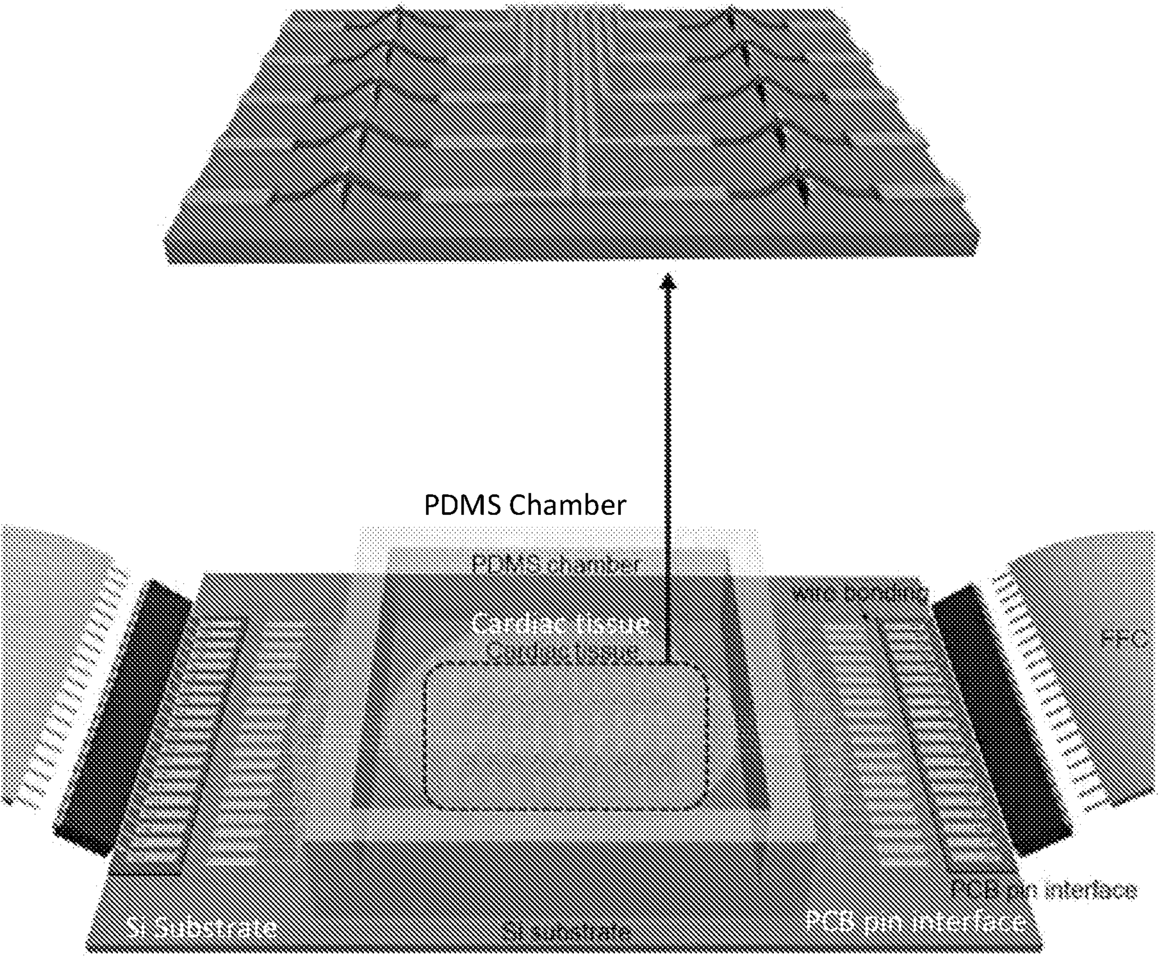
FIG. 8 shows arrays of exemplary biosensors integrated on a substrate in accordance with embodiments of the present disclosure.
Figure 9:
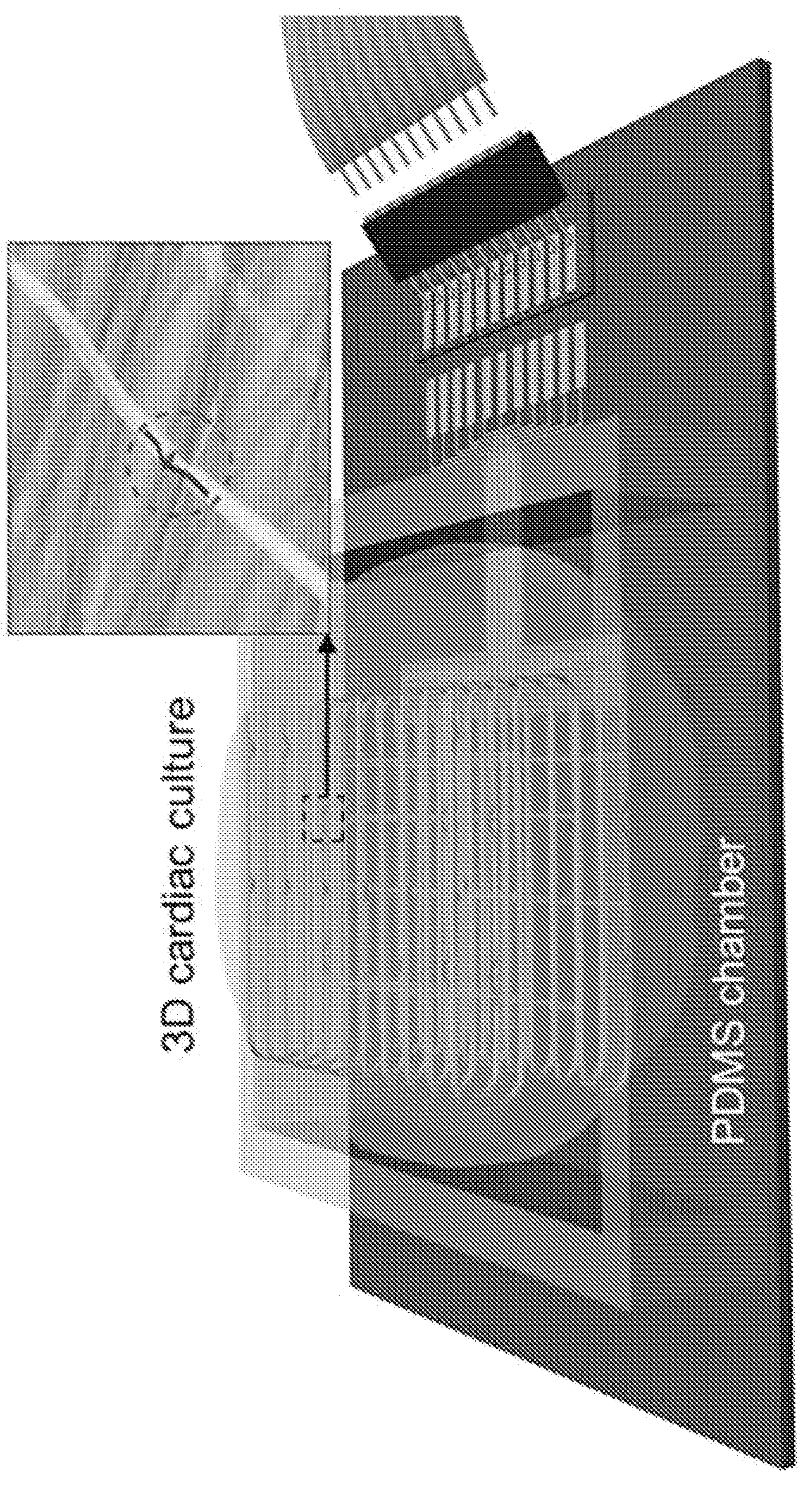
FIG. 9 shows biosensors integrated in a porous scaffold in accordance with various embodiments of the present disclosure.
Figure 10:
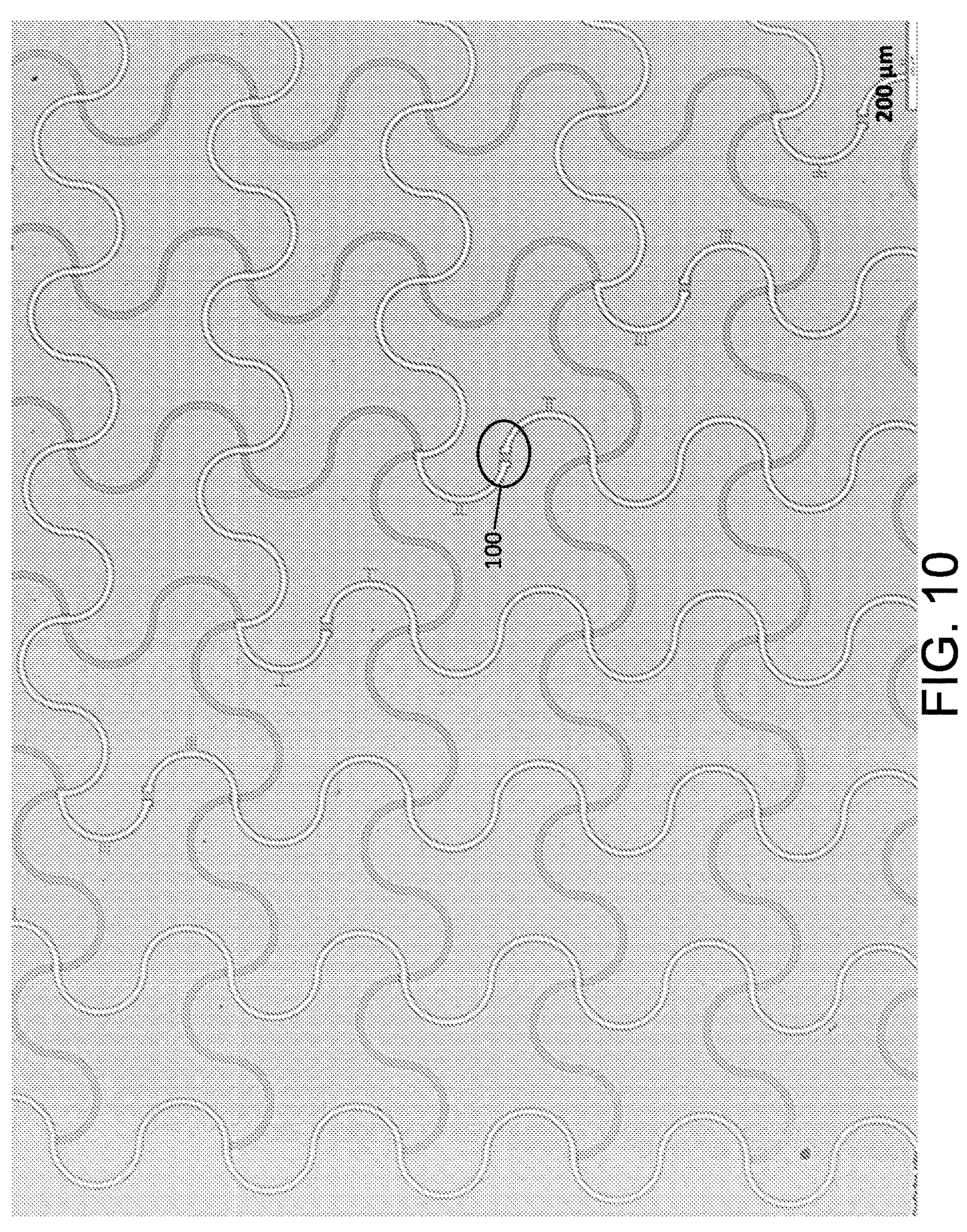
FIG. 10 shows a diagram of nanotransistor biosensors integrated on a flexible mesh scaffold before release from the substrate in accordance with embodiments of the present disclosure.
Figure 11A:
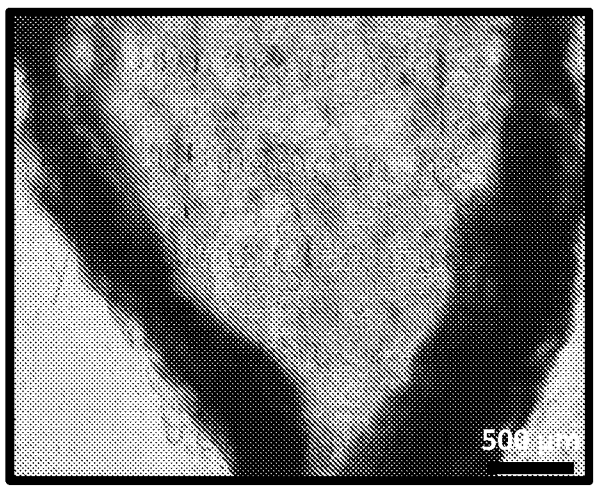
FIGS. 11A-11D show optical images of a flexible mesh system integrated with nanotransistor biosensors being embedded by cardiac tissue in accordance with embodiments of the present disclosure.
Figure 11B:
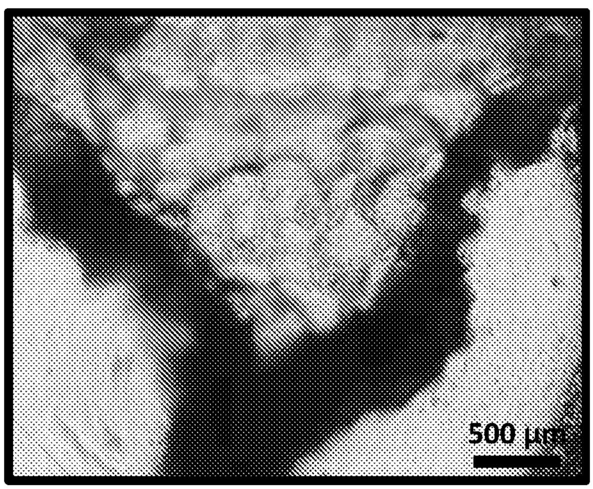
Figure 11C:
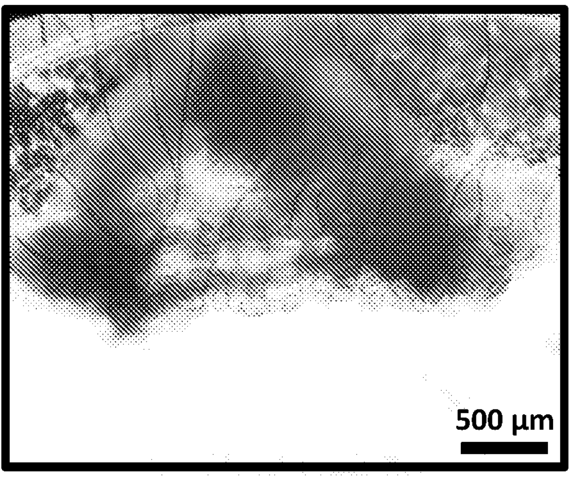
Figure 11D:
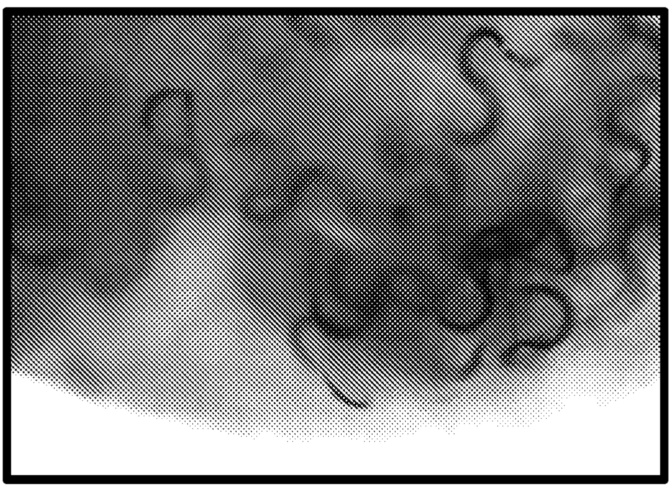
Figure 12:
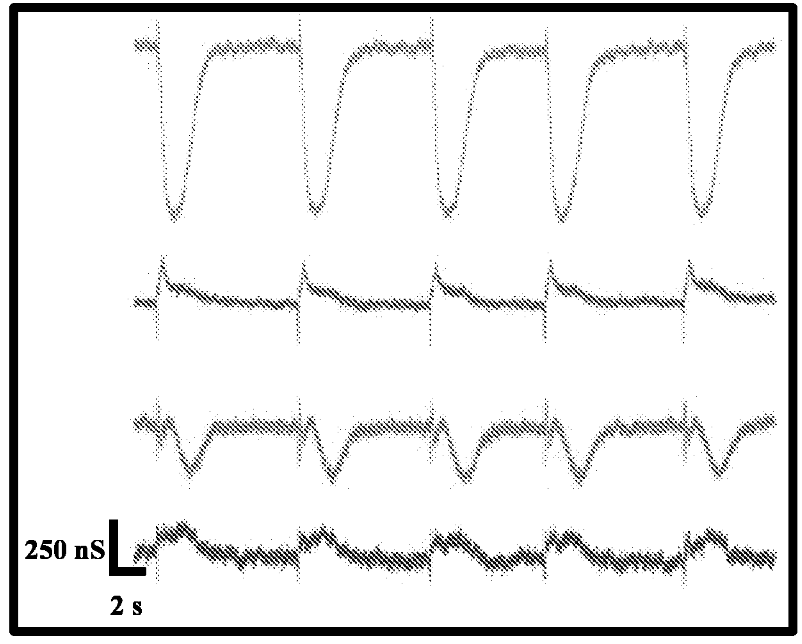
FIG. 12 shows electrical recordings obtained from the embedded biosensors of FIGS. 11A-11D.

In various embodiments, arrays of the 3D biosensors can be integrated on a substrate, as shown in FIG. 8. In this way, the sensor array can be used, but is not limited to only being used, to interface cardiac tissue for signal detection. The 3D sensors can be further integrated in a porous scaffold to realize 3D sensor innervation and detection, as shown in FIG. 9. Such an integrated porous and flexible sensor system can be implanted (e.g., as a biochip integrated circuit) in biological tissue (e.g., heart surface, deep muscle tissue) for in vivo sensing, monitoring, and cardiac disease diagnosis. As an example, nanotransistor biosensors can be integrated in a porous scaffold in the form of a flexible mesh scaffold, such as a mesh scaffold made from a polymeric ribbon substrate and metal interconnects. Accordingly, FIG. 10 shows a diagram of 3D nanotransistor biosensors 100 integrated on a flexible mesh scaffold before release from the substrate. This type of flexible mesh system can enable the intimated integration with 3D cardiac tissue, as shown in the following figures. To Illustrate, FIGS. 11A-11C are optical images showing the flexible mesh system being gradually engulfed by cardiac tissue over a three day period to form 3D integration during Day 1, Day 2, and Day 3, respectively. As a result, FIG. 11D is an enlarged optical image showing the integrated mesh after being fully embedded in the cardiac tissue. Correspondingly, FIG. 12 shows electrical recordings obtained from the embedded biosensors of FIGS. 11A-11D, which demonstrate that simultaneous recordings of electrical and mechanical responses from 3D cardiac tissues are enabled by exemplary 3D nanotransistor biosensors integrated on a flexible mesh scaffold.

In brief, the present disclosure presents 3D nanotransistor biosensors capable of simultaneously probing both mechanical and electrical cellular responses. The simultaneous electrical recordings enable the detailed tracking of cellular dynamics involving multiple biological processes at high spatiotemporal resolution, which are important for discerning cell states. The convergence of both functionalities in one device also helps to achieve 'equivalent scaling' to minimize invasiveness to tissue models. The 3D nanotransistors are capable of scalable integration on both biochips for in vitro models and deliverable substrates for in vivo implants.

Further, the present disclosure refers to experimental trials and various methods disclosed herein. Additional details on certain disclosed methods are provided below.

Si Nanowire Synthesis.

Si nanowires were grown by a vapor-liquid-solid (CVD) method described previously. Briefly, a Si substrate (Nova Electronic Materials) was cleaned by oxygen plasma (80 W, 1 min), immersed in a 0.1% (w/v) poly-L-lysine solution (Ted Pella) for 5 min, rinsed thoroughly with deionized water, and then immersed in the Au-nanoparticle solution (Ted Pella) for 5 min. The substrate with assembled Au nanoparticles was placed in a home-built CVD system for nanowire growth. The growth was carried out at 450° C. at a constant pressure of 30 torr with 2.5 standard cubic centimeters per minute (sccm) SiH4 (99.9999%; Voltaix), 3 sccm B2H6 (100 ppm in H2; Voltaix) and 10 sccm Ar (99.999%; Matheson) as reactant, dopant and carrier gases, respectively. The growth time was 60 min, producing an average length of ~40 μm.

3D Si Nanowire Assembly and Device Fabrication.

The 3D Si nanowire structures were assembled following methods developed previously. Assembled nanowire structures were defined with electrical contacts (Cr/Pd, 3/70 nm) using standard photolithography, metal evaporation, and lift-off processes. The contacts and interconnects were further passivated with a $Si_3N_4$ layer (~90 nm) to prevent current leakage in solution.

Cell Culture.

Cardiomyocytes were differentiated from human embryonic stem cells (hESCs, WAe009-A, H9) and human induced pluripotent stem cells (hiPSCs, generated from human primary T cells using episomal reprogramming) following methods described previously. Briefly, both cell types were maintained in the 60 mm tissue culture dishes coated with 10 ug/mL Matrigel in DMEM-F12 (Gibco™) using Essential 8 medium (Gibco™) and sub-passaged every 3-4 days. During differentiation, cells were seeded in a 12-well plate for 2-3 days until confluency, then replaced with RPMI 1640 medium (Gibco™) plus 1% B27-insulin (Gibco™) and 8 μM CHIR99021 (Tocris Bioscience™) (day 0). After 24 h (day 1), the medium was changed to RPMI 1640 plus 1% B27-insulin. On day 3, day 5, and day 7, the medium was changed to RPMI 1640 plus 1% B27-insulin and 5 μM IWR-1-endo (Cayman Chemical), RPMI 1640 plus 1% B27-insulin, and RPMI 1640 plus 1% B27, respectively. The medium was then replaced with RPMI 1640 plus 1% B27 every other day. The contraction of cells was usually observed on day 8. During days 10-15, cardiomyocytes were ready for experiments. The cells were rinsed with 1×DPBS to remove calcium and inhibit contraction, then incubated with 0.5 mL of 0.5 mM Trypsin-EDTA (Gibco™) for 5 mins in a 37° C. incubator to dissociate into single cells. The EDTA was then aspirated, and the cells were dissociated by gently pipetting with 2 mL RPMI 1640 plus 1% B27 using a 1 ml pipet tip. The cells were transferred to a 15 mL conical tube and centrifuged at 250 g for 3 minutes, then resuspended with 2 mL RPMI 1640 plus 1% B27 supplemented with 10% Fetal Bovine Serum (Gibco™) and 10 μM Y-27632 ROCK inhibitor (Tocris Bioscience™). The device substrate integrated with nanotransistors was sterilized by incubating in 70% ethanol solution (1 h) at room temperature and then UV-treated (1 h). The device was coated with 20 μg/mL Matrigel in RPMI 1640 for 1 h at 37° C. Cells were seeded on the device substrate at the density of 3-5×105/$cm^2$. The cardiomyocytes were maintained using RPMI 1640 plus 1% B27 by changing the medium daily. Electrical recordings were typically performed starting from day 5 after the cell seeding.

Electrical Measurements.

All in vitro electrical recordings were carried out at the ambient environment with an Au reference electrode. The conductance of the Si nanotransistors was measured with a DC bias set to 100 mV. The drain current was amplified with 12-channel home-built amplifier and the output data were collected at an acquisition rate of 30 kHz using a 16-channel A/D converter (Digidata 1440A; Molecular Devices) interfaced with a computer running pClamp 10.7 electrophysiology software (Molecular Devices, Axon Laboratory).

Imaging and Analysis.

The SEM images were acquired by a JSM-7001 F system. Bright-field optical videos of cell motion at 18 frame per second (FPS) were acquired through a Zeiss Axio Examiner microscope system, equipped with a CCD camera (AxioCam 702 Mono Camera) and Zen Blue software. The resolution of each frame was 1960×1080 pixels covering an imaging area of ~980×540 $\mu m^2$.

It should be emphasized that the above-described embodiments are merely possible examples of implementations, merely set forth for a clear understanding of the principles of the present disclosure. Many variations and modifications may be made to the above-described embodiment(s) without departing substantially from the principles of the present disclosure. All such modifications and variations are intended to be included herein within the scope of this disclosure.

Therefore, at least the following is claimed:

1. A biosensor device comprising:

a substrate;

a semiconductive channel member suspending between a pair of contacts on the substrate, wherein the semiconductive channel member comprises a convex protruding channel structure; and wherein the convex protruding channel structure is configured to simultaneously detect both electrical and mechanical cellular responses.

2. The biosensor device of claim 1, further comprising a mechanical support structure between the convex protruding channel structure and the substrate that physically supports the convex protruding channel structure.

3. The biosensor device of claim 1, wherein the semiconductive channel member comprises a semiconducting nanowire.

4. The biosensor device of claim 3, wherein the semiconductive channel member comprises a silicon nanowire.

5. The biosensor device of claim 1, wherein the semiconductive channel member comprises a semiconducting nanoribbon.

6. The biosensor device of claim 5, wherein the semiconductive channel member comprises graphene material or Molybdenum disulfide ($MoS_2$).

7. The biosensor device of claim 5, wherein the semiconductive channel member comprises a silicon nanoribbon.

8. The biosensor device of claim 1, wherein the semiconductive channel member comprises a stack of nanoribbons.

9. The biosensor device of claim 1, wherein the semiconductive channel member comprises a stack of nanoribbons, wherein a top layer of the stack is configured to detect the electrical cellular response and a bottom layer of the stack is configured to detect the mechanical cellular response.

10. The biosensor device of claim 1, wherein the biosensor device is integrated in an array of biosensor devices on the substrate.

11. The biosensor device of claim 10, wherein the array of biosensor devices is integrated in a porous scaffold structure.

12. The biosensor device of claim 1, wherein a size of the biosensor device is smaller than that of a cardiac cell.

13. The biosensor device of claim 1, wherein the electrical cellular response is detected via a field effect and the mechanical cellular response is detected via a piezoresistive effect.

14. A biosensing method comprising:

positioning a biosensor device under biological tissue, wherein the biosensor device comprises:

a substrate; and a semiconductive channel member suspending between a pair of contacts on the substrate, wherein the semiconductive channel member comprises a convex protruding channel structure;

detecting an electrical cellular response of the biological tissue that is sensed by the biosensor device via a field effect; and detecting a mechanical cellular response of the biological tissue that is sensed by the biosensor device via a piezoresistive effect simultaneously with the detection of the electrical cellular response of the biological tissue.

15. The biosensing method of claim 14, wherein the biological tissue comprises muscle tissue.

16. The biosensing method of claim 15, wherein the biological tissue comprises cardiac tissue.

17. The biosensing method of claim 14, further comprising identifying a cardiac event based on the detected electrical cellular response and the detected mechanical cellular response.

18. The biosensing method of claim 14, further comprising identifying a drug effect based on the detected electrical cellular response and the detected mechanical cellular response.

19. The biosensing method of claim 14, wherein the semiconducting channel member comprises a silicon nanowire.

20. The biosensing method of claim 14, wherein the semiconducting channel member comprises a silicon nanoribbon.

* * * * *